US012600750B2

(12) United States Patent
Zheng et al.

(10) Patent No.: US 12,600,750 B2
(45) Date of Patent: Apr. 14, 2026

(54) METHODS FOR INACTIVATING AND STORING RESPIRATORY SYNCYTIAL VIRUS

(71) Applicants: Xiamen University, Xiamen (CN); Xiamen Innovax Biotech Co., Ltd., Xiamen (CN)

(72) Inventors: Zizheng Zheng, Xiamen (CN); Wei Zhang, Xiamen (CN); Lujing Zhang, Xiamen (CN); Yongpeng Sun, Xiamen (CN); Li Chen, Xiamen (CN); Ningshao Xia, Xiamen (CN)

(73) Assignees: Xiamen University, Xiamen (CN); Xiamen Innovax Biotech Co., Ltd., Xiamen (CN)

( * ) Notice: Subject to any disclaimer, the term of this patent is extended or adjusted under 35 U.S.C. 154(b) by 1260 days.

(21) Appl. No.: 17/258,109

(22) PCT Filed: Jul. 8, 2019

(86) PCT No.: PCT/CN2019/095113
§ 371 (c)(1),
(2) Date: Aug. 4, 2021

(87) PCT Pub. No.: WO2020/007371
PCT Pub. Date: Jan. 9, 2020

(65) Prior Publication Data
US 2022/0009969 A1 Jan. 13, 2022

(30) Foreign Application Priority Data
Jul. 6, 2018 (CN) .......................... 201810737479.5

(51) Int. Cl.
| A61K 39/00 | (2006.01) |
| A61K 39/155 | (2006.01) |
| A61P 31/14 | (2006.01) |
| C07K 14/005 | (2006.01) |
| C12N 1/04 | (2006.01) |
| C12N 7/00 | (2006.01) |

(52) U.S. Cl.
CPC .......... *C07K 14/005* (2013.01); *A61K 39/155* (2013.01); *A61P 31/14* (2018.01); *C12N 1/04* (2013.01); *C12N 7/00* (2013.01); *A61K 2039/5252* (2013.01); *C12N 2760/18534* (2013.01); *C12N 2760/18561* (2013.01); *C12N 2760/18563* (2013.01); *C12N 2760/18571* (2013.01)

(58) Field of Classification Search
CPC ............... C07K 14/005; A61K 39/155; A61K 2039/5252; A61K 2039/575; A61K 39/12; A61P 31/14; A61P 11/00; C12N 1/04; C12N 7/00; C12N 2760/18534; C12N 2760/18561; C12N 2760/18563; C12N 2760/18571
See application file for complete search history.

(56) References Cited

U.S. PATENT DOCUMENTS

| 6,309,650 | B1 | 10/2001 | Kim et al. |
| 2010/0061965 | A1 | 3/2010 | Connolly et al. |
| 2010/0291147 | A1 | 11/2010 | Baudoux et al. |
| 2014/0271696 | A1 | 9/2014 | De Haan et al. |
| 2014/0271699 | A1 | 9/2014 | Kwong et al. |
| 2015/0166610 | A1 | 6/2015 | Baudoux et al. |
| 2016/0031972 | A1 | 2/2016 | Zheng et al. |

FOREIGN PATENT DOCUMENTS

| CN | 1295480 | A | 5/2001 |
| CN | 1505478 | A | 6/2004 |
| CN | 101952321 | A | 1/2011 |
| CN | 102099054 | A | 6/2011 |
| CN | 105319373 | A | 2/2016 |
| CN | 105722856 | A | 6/2016 |
| CN | 107029227 | A | 8/2017 |
| CN | 108300705 | A | 7/2018 |
| CN | 105722856 | B | 4/2019 |
| JP | 2001-514844 | A | 9/2001 |
| WO | WO 99/40937 | A2 | 8/1999 |
| WO | WO 02/069887 | A2 | 9/2002 |
| WO | WO 2014/160463 | A1 | 10/2014 |
| WO | WO 2015/013551 | A1 | 1/2015 |
| WO | WO 2018/130072 | A1 | 7/2018 |

OTHER PUBLICATIONS

Sawada and Nakayama (2016). Experimental animal model for analyzing immunobiological responses following vaccination with formalin-inactivated respiratory syncytial virus. Microbiol Immunol 2016; 60: 234-242 (Year: 2016).*
Killikelly et al (2016). Pre-fusion F is absent on the surface of formalin-inactivated respiratory syncytial virus. Scientific Reports. 6: 34108. (Year: 2016).*
Chen et al (2023). Gamma Irradiation-Inactivated Respiratory Syncytial Virus Vaccine Provides Protection but Exacerbates Pulmonary Inflammation by Switching from Prefusion to Postfusion F Protein. Microbiol Spectr. Aug. 17, 2023; 11(4): e0135823. (Year: 2023).*

(Continued)

*Primary Examiner* — Bennett M Celsa
*Assistant Examiner* — Samadhan Jaising Jadhao
(74) *Attorney, Agent, or Firm* — Wolf, Greenfield & Sacks, P.C.

(57) ABSTRACT

Provided are a method for inactivating respiratory syncytial virus (RSV) and stabilizing pre-F protein in RSV and inactivated RSV virus obtained thereby. Also provided are a vaccine comprising the inactivated RSV virus and a use of the vaccine in preventing or treating RSV infection or a disease related thereto.

19 Claims, 13 Drawing Sheets

Specification includes a Sequence Listing.

(56)                   References Cited

OTHER PUBLICATIONS

Moller et al (2015). Evaluation of Virus Inactivation by Formaldehyde to Enhance Biosafety of Diagnostic Electron Microscopy. Viruses 2015, 7, 666-679. (Year: 2015).*

Kiernan (2000). Formaldehyde, Formalin , Paraformaldehyde and Glutaraldehyde. Microscopy Today, 00-1, pp. 8-12. (Year: 2000).*

Elveborg et al (2022) Methods of Inactivation of Highly Pathogenic Viruses for Molecular, Serology or Vaccine Development Purposes. Pathogens 2022, 11, 271. (Year: 2022).*

Haynes et al (2003). Enhanced disease and pulmonary eosinophilia associated with formalin-inactivated respiratory syncytial virus vaccination are linked to G glycoprotein CX3C-CX3CR1 interaction and expression of substance P. J Virol. Sep. 2003;77(18):9831-44. (Year: 2003).*

De Swart et al (2002). Immunization of macaques with formalin-inactivated respiratory syncytial virus (RSV) induces interleukin-13-associated hypersensitivity to subsequent RSV infection. J Virol. Nov. 2002; 76(22): 11561-9. (Year: 2002).*

Chaiwatpongsakorn S, Epand RF, Collins PL, Epand RM, Peeples ME. Soluble respiratory syncytial virus fusion protein in the fully cleaved, pretriggered state is triggered by exposure to low-molarity buffer. J Virol. Apr. 2011;85(8):3968-77. (Year: 2011).*

Brown et al (2004). Analysis of the interaction between respiratory syncytial virus and lipid-rafts in Hep2 cells during infection. Virology 327 (2004) 175-185. (Year: 2004).*

Wu et al (2017). Inactivation of rabies virus. Journal of Virological Methods 243 (2017) 109-112 (Year: 2017).*

Creager et al (2017). 3.18 Immunohistochemistry. p. 388-405. 2017 Elsevier Ltd. (Year: 2017).*

Clemens R, Safary A, Hepburn A, Roche C, Stanbury WJ, André FE. Clinical experience with an inactivated hepatitis A vaccine. J Infect Dis. Mar. 1995; 171 Suppl 1:S44-9. (Year: 1995).*

Wilton T, Dunn G, Eastwood D, Minor PD, Martin J. Effect of formaldehyde inactivation on poliovirus. J Virol. Oct. 2014;88(20):11955-64. (Year: 2014).*

Furesz, J., Scheifele, D. W. & Palkonyay, L. Safety and effectiveness of the new inactivated hepatitis A virus vaccine. CMAJ: Canadian Medical Association Journal 152, 343-348 (1995). (Year: 1995).*

Sanders B, Koldijk M, Schuitemaker H. Inactivated Viral Vaccines. Vaccine Analysis: Strategies, Principles, and Control. Nov. 28, 2014:45-80. (Year: 2014).*

Moghaddam et al. (2006). A potential molecular mechanism for hypersensitivity caused by formalin-inactivated vaccines. Nat Med 12, 905-907. (Year: 2006).*

Al-Afif A, Alyazidi R, Oldford SA, Huang YY, King CA, Marr N, Haidl ID, Anderson R, Marshall JS. Respiratory syncytial virus infection of primary human mast cells induces the selective production of type I interferons, CXCL10, and CCL4. J Allergy Clin Immunol. Nov. 2015; 136(5):1346-54.e1. (Year: 2015).*

Hulskotte EG, Dings ME, Norley SG, Osterhaus AD. Chemical inactivation of recombinant vaccinia viruses and the effects on antigenicity and immunogenicity of recombinant simian immunodeficiency virus envelope glycoproteins. Vaccine. Dec. 1997; 15(17-18):1839-45. (Year: 1997).*

Kiernan, J.A. Formaldehyde, Formalin, Paraformaldehyde and Glutaraldehyde: What They are and What They Do. Microsc. Today 2000, 8, 8-13. (Year: 2000).*

Killikelly AM, Kanekiyo M, Graham BS. (2016). Pre-fusion F is absent on the surface of formalin-inactivated respiratory syncytial virus. Sci Rep. Sep. 29, 2016;6:34108. (Year: 2016).*

Extended European Search Report for Application No. 19830461.0, mailed Mar. 30, 2022.

Japanese Office Action for Application No. 2021-521873, mailed Jun. 6, 2023.

Chaiwatpongsakorn, Soluble Respiratory Syncytial Virus Fusion Protein in the Fully Cleaved, Pretriggered State, a Tool to Study Protein Triggering. The Ohio State University, The Comparative and Veterinary Medicine Graduate Program Dissertation. 2011. 160 pages.

International Search Report and Written Opinion for Application No. PCT/CN2019/095113, mailed Oct. 9, 2019.

International Preliminary Report on Patentability for Application No. PCT/CN2019/095113, mailed Jan. 21, 2021.

Office Action for Chinese Application No. 201711447827.7, mailed Jul. 28, 2020.

Fu et al., Advances in Live Vector-based Vaccines Against Respiratory Syncytial Virus. China Biotechnology. Dec. 2012; 32(1):92-96.

Killikelly et al., Pre-fusion F is absent on the surface of formalin-inactivated respiratory syncytial virus. Sci Rep. Sep. 29, 2016;6:34108. doi: 10.1038/srep34108.

Stott et al., Exploration of Purification Conditions of HRSV and Preliminary Evaluation of Experimental Vaccine Immunogenicity. Foreign Medical Sciences. Dec. 27, 1986; 6: 5-57.

Trudel et al., Identification of a synthetic peptide as part of a major neutralization epitope of respiratory syncytial virus. J Gen Virol. Sep. 1987;68 (Pt 9):2273-80. doi: 10.1099/0022-1317-68-9-2273.

Baer et al., Viral concentration determination through plaque assays: using traditional and novel overlay systems. J Vis Exp. Nov. 4, 2014:(93):e52065. doi: 10.3791/52065.

Racaniello, Detecting viruses: the plaque assay. Virology Blog. Jul. 6, 2009. 1 page. Accessed at: https://virology.ws/2009/07/06/detecting-viruses-the-plaque-assay, [last accessed: Oct. 9, 2025].

* cited by examiner

Input:100ul

A

B

A

B

A

B

A

B

SEQUENCE LISTING

<160> NUMBER OF SEQ ID NOS: 1

<210> SEQ ID NO 1
<211> LENGTH: 574
<212> TYPE: PRT
<213> ORGANISM: respiratory syncytial virus

<400> SEQUENCE: 1

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

-continued

```
Tyr Gly Lys Thr Lys Cys Thr Ala Ser Asn Lys Asn Arg Gly Ile Ile
            420             425                 430

Lys Thr Phe Ser Asn Gly Cys Asp Tyr Val Ser Asn Lys Gly Met Asp
        435             440                 445

Thr Val Ser Val Gly Asn Thr Leu Tyr Tyr Val Asn Lys Gln Glu Gly
    450             455                 460

Lys Ser Leu Tyr Val Lys Gly Glu Pro Ile Ile Asn Phe Tyr Asp Pro
465             470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515             520                 525

Thr Ile Ile Ile Val Ile Ile Val Ile Leu Leu Ser Leu Ile Ala Val
    530             535                 540

Gly Leu Leu Leu Tyr Cys Lys Ala Arg Ser Thr Pro Val Thr Leu Ser
545             550                 555                 560

Lys Asp Gln Leu Ser Gly Ile Asn Asn Ile Ala Phe Ser Asn
            565                 570
```

METHODS FOR INACTIVATING AND STORING RESPIRATORY SYNCYTIAL VIRUS

RELATED APPLICATIONS

This application is a national stage filing under 35 U.S.C. § 371 of International PCT Application PCT/CN2019/095113, filed Jul. 8, 2019, which claims priority to Chinese Patent Application No. 201810737479.5, filed Jul. 6, 2018, the entire contents of each of which is incorporated herein by reference.

TECHNICAL FIELD

The present application relates to the field of virology and immunology. Specifically, the present application relates to a method for inactivating an isolated respiratory syncytial virus (RSV) and stabilizing a pre-F protein in the RSV. In addition, the present application also relates to a method for preserving a RSV and stabilizing a pre-F protein in the RSV. The present application also relates to a vaccine comprising an inactivated RSV, in which the inactivated RSV is prepared and/or preserved by the method of the present invention, and use of the vaccine for prevention or treatment of RSV infection or a disease associated with RSV infection.

BACKGROUND ART human respiratory syncytial virus (RSV) has been the most important pathogen of lower respiratory tract infections in infants and young children since its discovery in the 1950s. In the United States, RSV is the leading cause of hospitalization in infants under 1 year of age (D. K. Shay, R. C. Holman. et al., JAMA, 282 (1999) 1440-1446) and one of the main reasons for clinical appointments in children under 5 years of age (C. B. Hall, G. A. Weinberg, et al., N Engl J Med, 360 (2009) 588-598). Globally, there are more than 30 million cases of lower respiratory tract infection caused by RSV every year, and more than 3 million people need to be hospitalized. RSV is the most common cause of hospitalization in children under 5 years of age (H. Nair, W. A. Brooks, et al., Lancet, 378 (2011) 1917-1930). The RSV infection rate in premature infants, as well as infants and young children with bronchial and lung dysplasia, congenital heart disease and immunodeficiency is as high as 50% to 70% (A. C. Cooper, N. C. Banasiak, P. J. Allen, Pediatr Nurs, 29 (2003) 452-456). There are 160,000 to 600,000 child deaths each year related to RSV (T. S. Howard, L. H. Hoffman, et al. J Pediatr, 137 (2000) 227-232; S. Leader, K. Kohlhase. J Pediatr, 143 (2003) S127-132). The length of hospitalization for infants and young children infected with RSV can be up to 2.5 months, and the related medical expenses caused thereby can be as high as US$360-570 million per year in the United States (E. A. Simoes. Lancet, 354 (1999) 847-852). The older persons are also susceptible to RSV. The number of elderly deaths caused by RSV infection each year is more than 12,000, which is about ⅓ of the influenza mortality rate in the same population (A. R. Falsey, P. A. Hennessey, et al. N Engl J Med, 352 (2005) 1749-1759; W. W. Thompson, D. K. Shay, E. Weintraub, et al. JAMA, 289 (2003) 179-186). In China, due to the lack of domestically developed RSV diagnostic reagents, RSV testing cannot be promoted due to high costs. This has led to the prevalence and harmfulness of RSV in China is still not fully understood. However, studies in some regions in China have shown that RSV infection is also an important cause of lower respiratory tract infections in Chinese children (Xu Guanren, Sun Songwen, Xu Xuqing, et al. Journal of Disease Control, 4 (2000) 37-39; Xie Jianping, Xie Jianping, He Cuijuan, et al. Chinese Journal of Pediatrics, 35 (1997) 402-403; Zhu Runan, Deng Jie, Wang Fang, et al. 21 (2003) 25-28).

In the 1860s, the protective efficiency of FI-RSV (formalin-inactivated whole virus vaccine, by intramuscular injection, with aluminum as the adjuvant) had been evaluated in infants and children. However, the results showed that the vaccine lacked protection in subsequent natural RSV infections and even caused an increase in severity of the disease. The fact that the vaccine caused increase in severity of the disease severely blocked the development of RSV vaccines. So far, there is no anti-RSV vaccine that can provide effective protection. At present, only one neutralization antibody (Palivizumab, trade name: Synagis) that recognizes RSV fusion protein can produce passive immunity in newborns and reduce the incidence in newborns. The application of Syangis shows that the neutralizing monoclonal antibody that binds to RSV-F protein can be used for clinical protection, and there are effective neutralizing active sites on the F protein. The F protein is located on the surface of the virus and is necessary for virus entry and syncytia formation. Therefore, the F protein is an important target protein for developing anti-RSV vaccines and screening preventive and protective antibodies.

RSV is a single-stranded, negative-sense, non-segmented RNA virus belonging to the genus Pneumoviridae of Paramyxoviridae. Its genome has 15,222 nucleotides and encodes 10 main proteins; among them, F protein (Fusion protein) is a N-glycosylated type I transmembrane glycoprotein having a full length of 574 amino acids, and as the main transmembrane protein, it is an important surface molecule in the process of RSV infection. The mechanism and process of membrane fusion triggered by F protein are still unclear. McLellan et al. had obtained a stable post-F protein structure by using mammalian expression system (J. S. McLellan, M. Chen, J. S. Chang, et al. J Virol, 84 (2010) 12236-12244). For pre-F protein, because its structure is unstable and there are many intermediates, it is quite difficult to study the structure of pre-F protein by preparing its crystals. McLellan et al. (ibid.) used the HPIV3 pre-F protein with known structure to simulate and predict the structure of the RSV pre-F protein, and proposed that the RSV F protein might have a pre-F conformation. In addition, McLellan et al. (ibid.) also proposed that after F protein binds to target cells, its conformation changes from a high-energy, metastable state conformation of pre-fusion F protein (pre-fusion F, pre-F) to a highly stable conformation of post-fusion F protein (post-fusion F, post-F), which leads to the fusion of the viral membrane and the cell membrane. The free energy of the metastable pre-F conformation and the stable post-F conformation are very different, which makes the process of membrane fusion irreversible.

In addition, the neutralizing epitopes on the conformations of pre-F and post-F proteins have also been identified. The results show that pre-F and post-F proteins share about 50% of the protein surface, and epitopes with high neutralizing activity (strong neutralizing epitopes) such as siteφ are mainly distributed on the pre-F conformation, while the post-F conformation mainly comprises epitopes with weaker neutralizing activity (weakly neutralizing epitopes), such as site II and site IV (see FIG. 1).

These research results show that compared with post-F protein, pre-F protein has more and stronger neutralizing epitopes, and thus has a higher potential for use as a vaccine.

However, because the pre-F protein is in a metastable state and is easily converted into a stable post-F protein, there are still great difficulties and challenges in developing an effective vaccine from the pre-F protein. There is a need in the art for a method to develop, stabilize and maintain a pre-F protein in an inactivated and isolated RSV, so as to improve the effectiveness of the inactivated RSV as a vaccine.

CONTENTS OF THE PRESENT INVENTION

In the present invention, unless otherwise specified, the scientific and technical terms used herein have the meanings commonly understood by those skilled in the art. In addition, the laboratory procedures of cell culture, molecular genetics, nucleic acid chemistry, and immunology used herein are all routine procedures widely used in the corresponding fields. Meanwhile, in order to better understand the present invention, definitions and explanations of related terms are provided below.

As used herein, the term "RSV fusion protein" or "F protein" refers to Fusion protein (F protein) of respiratory syncytial virus (RSV), which is well known to those skilled in the art and the exemplary amino acid sequence of which may refer to, for example, NCBI GENBANK database accession number: P03420. In the context, "RSV fusion protein", "fusion protein" and "F protein" are used interchangeably.

As used herein, when referring to the amino acid sequence of F protein, it is descried by using the sequence shown in SEQ ID NO:1. For example, the expression "amino acid residues 196-209 of F protein" refers to amino acid residues 196-209 of the polypeptide shown in SEQ ID NO:1. However, those skilled in the art understand that in the amino acid sequence of F protein, mutations or variations (including but not limited to, substitutions, deletions, and/or additions, such as F protein of different genotypes or subtypes) can be naturally generated or artificially introduced without affecting its biological functions. Therefore, in the present invention, the term "F protein" shall include all such sequences, including, for example, the sequence shown in SEQ ID NO:1 and its natural or artificial variants. Moreover, when describing the sequence fragment of F protein, it includes not only the sequence fragments of SEQ ID NO:1, but also the corresponding sequence fragments in its natural or artificial variants. For example, the expression "amino acid residues 196-209 of F protein" includes amino acid residues 196-209 of SEQ ID NO:1, and corresponding fragments in its (natural or artificial) variants. According to the present invention, the expression "corresponding sequence fragments" or "corresponding fragments" refers to the fragments that are located in equivalent positions of the sequences being compared when the sequences are optimally aligned, i.e. the sequences are aligned to obtain a highest percentage of identity.

Previous studies have shown that F protein has at least one definite conformation, post-F. In combination with the research results of F protein of parainfluenza virus (PIV), McLellan et al. speculated that the F protein of RSV might have a pre-F conformation (McLellan et al. (2010), J Vriol, 84: 12236-12244). Under normal circumstances, the pre-F conformation is unstable and it will spontaneously transform into a stable post-F conformation. Therefore, the F protein expressed and purified from the cell is present mainly in the post-F conformation; and, in the inactivated RSV, the F protein is present also mainly in the post-F conformation.

As used herein, the term "pre-F protein" refers to an F protein that exists in a pre-F conformation. As used herein, the term "post-F protein" refers to an F protein that exists in a post-F conformation. For more detailed descriptions of pre-F protein, post-F protein and their conformations, please refer to McLellan et al. (2010), J Vriol, 84: 12236-12244; McLellan et al. (2013), Science, 340: 1113-1117; McLellan et al. (2015), Curr Opin Virol, 11: 70-75; Chinese patent application 201480013927.7, and PCT international application PCT/CN2014/073505 (their full texts are incorporated herein by reference for all purposes). In the context, "pre-F" and "pre-Fusion" are used interchangeably; "post-F" and "post-Fusion" are used interchangeably.

As used herein, the expression "stabilizing pre-F protein" refers to at least partially inhibiting, reducing or delaying the conversion of pre-F protein to post-F protein. In addition, this expression also refers to maintaining the pre-F conformation of F protein as much as possible to avoid its conversion to the post-F conformation.

As one of the most important surface structural proteins of viruses, F protein has a large number of neutralization antibody recognition epitopes on its surface. The currently known neutralization antibodies of RSV F protein mainly target the following epitopes (J. S. McLellan, Y. Yang, et al. J Virol, 85 (2011) 7788-7796; and, M. Magro, D. Andreu, et al. al. J Virol, 84 (2010) 7970-7982):

Site II epitope: The antibodies against Site II epitope include the marketed prophylactic monoclonal antibody Synagis and its equivalent derivatives motavizumab and 47F; they mainly recognize aa 255-275 of F protein. McLellan et al. (J. S. McLellan, M. Chen, J. S. Chang, et al. J Virol, 84 (2010) 12236-12244) confirmed by analyzing the crystal structure of the complex of motavizumab monoclonal antibody and F protein peptide aa 254-277 that the region formed a "helix-turn-helix" secondary structure. The crystal structure showed that motavizumab monoclonal antibody bound to one end of the "helix-turn-helix" structure, and made hydrogen bond and ionic bond act on Asn at position 268 and Lys at position 272. Further studies showed that mutations at these two positions could cause antibody escape. The structure of the Site II epitope bound by motavizumab was very intact in the post-F conformation, and the antibody binding site was fully exposed. The structure of motavizumab and post-F protein revealed the mechanism by which Synagis and motavizumab monoclonal antibody had neutralizing activity. The simulated structure of the RSV pre-F protein showed that the epitope was inside the pre-F protein conformation and could not be exposed on the surface of the pre-F protein. Graham et al. confirmed that Synagis and motavizumab monoclonal antibody could only inhibit the fusion of RSV and cells, but not the adsorption of RSV (J. S. McLellan, Y. Yang, et al. J Virol, 85 (2011) 7788-7796; J. S. McLellan, M. Chen, A. Kim, et al. Nat Struct Mol Biol, 17 (2010) 248-250).

Site I epitope: The antibodies that recognize the Site I epitope include 131-2a, which recognizes the cysteine-rich region of the F protein. Such antibodies block up to 50% of RSV infection, indicating that the epitope has post-translational heterogeneity, or that these antibodies have a neutralizing effect through indirect effects (e.g., viral aggregation). In addition, these antibodies partially block the adsorption of virus to target cells. The Site I epitope is close to the cell membrane of the virus in the conformation of the pre-F protein, but is located at the apex in the conformation of the post-F protein.

Site IV epitope: Site IV epitope is the target of monoclonal antibody antibodies such as 19 and 101F, which are mainly involved in the aa 422-438 of F protein. This epitope is located in a relatively conserved region in the F protein.

McLellan et al. (J. S. McLellan, Y. Yang, et al. J Virol, 85 (2011) 7788-7796) have identified the crystal structure of the complex of 101F and F protein peptide (aa 422-438). The results showed that the core region of Site IV epitope was aa 427-437.

Site φ epitope: Site φ epitope is the target of pre-F specific antibodies D25, AM22 and 5C4. McLellan et al. (McLellan J. S., Chen M, et al. Science 2013, 340:1113-1117) analyzed the structure of the complex of pre-F specific antibody and pre-F and found that this epitope was involved in the loose area (aa 62-69) of F protein and α4 helix (aa 196-209) of F protein. In addition, the research results also showed that when the F protein was transformed from pre-F to post-F conformation, the epitope shifted by at least 5 Å, and the α4 helix was converted by 180°. Therefore, the antibodies that recognized this epitope were pre-F specific antibodies and could not recognize the post-F protein.

Previous research results (McLellan J. S., Chen M, et al. Science 2013, 340: 1113-1117) have shown that Site φ epitope had high neutralizing activity and was mainly distributed in the pre-F conformation; Site II epitope and Site IV epitope had relatively weak neutralizing activity and was distributed in both pre-F and post-F conformations (FIG. 1).

As used herein, the term "epitope" refers to a site on an antigen that is specifically bound by an immunoglobulin or antibody. "Epitope" is also called "antigenic determinant" in the art. Epitope or antigenic determinant usually consists of chemically active surface groups of molecules such as amino acids or carbohydrates or sugar side chains and usually has specific three-dimensional structural characteristics and specific charge characteristics. For example, an epitope usually includes at least 3, 4, 5, 6, 7, 8, 9, 10, 11, 12, 13, 14 or 15 contiguous or non-contiguous amino acids in a unique spatial conformation, which can be "linear" or "conformational". See, for example, Epitope Mapping Protocols in Methods in Molecular Biology, Vol. 66, G. E. Morris, Ed. (1996). In a linear epitope, all interaction points between a protein and a molecule that interacts with it (e.g., an antibody) exist linearly along the protein's primary amino acid sequence. In a conformational epitope, interaction points exist across protein amino acid residues that are separated from each other.

As used herein, the term "specific binding" refers to a non-random binding reaction between two molecules, such as the reaction between an antibody and an antigen to which it is directed. In some embodiments, an antibody that specifically binds to a certain antigen (or an antibody has specificity to a certain antigen) refers to that the antibody binds to the antigen with an affinity ($K_D$) of less than about $10^{-5}$ M, such as less than about $10^{-6}$ M, $10^{-7}$ M, $10^{-8}$ M, $10^{-9}$ M, or $10^{-10}$ M or less.

As used herein, the term "$K_D$" refers to a dissociation equilibrium constant of a specific antibody-antigen interaction, which is used to describe the binding affinity between the antibody and the antigen. The smaller the dissociation equilibrium constant, the tighter the antibody-antigen binding, and the higher the affinity between the antibody and the antigen. Generally, an antibody binds to an antigen with a dissociation equilibrium constant ($K_D$) of less than about $10^{-5}$ M, for example, less than about $10^{-6}$ M, $10^{-7}$ M, $10^{-8}$ M, $10^{-9}$ M, or $10^{-10}$ M or less, for example, as measured in by BIACORE instrument using surface plasmon resonance method (SPR).

As used herein, the term "neutralizing epitope" refers to an epitope that can induce a neutralizing activity against virus in a body. Such epitopes not only participate in the recognition of viral proteins by the immune system (e.g., antibodies), but also usually induce the immune system of the body to produce antibodies with neutralizing activity (i.e., neutralization antibodies). As used herein, "neutralization antibody" refers to an antibody that can significantly reduce or completely inhibit the virulence (e.g., the ability to infect cells) of a target virus. Generally speaking, a neutralization antibody can recognize and bind to a neutralizing epitope on a target virus, and prevent the target virus from entering/infecting the cells of a subject. As used herein, the neutralizing activity of an epitope refers to an ability of the epitope to induce the body to produce a neutralizing activity against a virus. The higher the neutralizing activity of the epitope, the stronger its ability to induce the body to produce neutralizing activity against the virus.

As used herein, the term "host cell" refers to a cell capable of being infected with RSV and allowing proliferation of RSV therein. Such host cells may be adherent cells or suspension cells, and include primary cells and established cell lines. Examples of such host cells include, but are not limited to, respiratory epithelial cell, liver cell, lung cell, kidney cell, cervical cell, ovarian cell, bone cell, breast cell, striated muscle cell, gastric epithelial cell, skin epidermal cell, fibroblast and prostate cell of a mammal (e.g., rodent and primate, such as mouse, monkey, and human); such as Hep-2 cell, CNE1 cell, CNE2 cell, BEL-7404 cell, BEL-7402 cell, QSG-7701 cell, PLC/PRF/5 cell, Huh7 cell, Huh7.5.1 cell, SSMC-7721 cell, BNL-HCC cell, Hep3B, SNU-739 cell, TIB75 cell, A549 cell, H480 cell, H1299 cell, H441 cell, H368 cell, H1335 cell, H23 cell, L929 cell, 293FT cell, 293T cell, 293β5 cell, Vero cell, BHK-MKL cell, RK-13 cell, HeLa cell, TZM-bl cell, SK-OV-3 cell, U2-OS cell, 143B cell, MCF-7 cell, MDA-MB-231 cell, T-47D cell, RD cell, BGC-823 cell, AGS cell, A431NS cell, MeWo cell, LNCap cell, RM1 cell and PC-3 cell.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg-.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the terms "monoclonal antibody" and "mAb" have the same meaning and can be used interchangeably; the terms "polyclonal antibody" and "pAb" have the same meaning and can be used interchangeably; and the terms "polypeptide" and "protein" have the same meaning and can be used interchangeably. In addition, in the present invention, amino acids are usually represented by one-letter and three-letter abbreviations well known in the art. For example, alanine can be represented by A or Ala.

As used herein, the term "pharmaceutically acceptable carrier and/or excipient" refers to a carrier and/or excipient that is pharmacologically and/or physiologically compatible with a subject and an active ingredient, which is well known in the art (see, for example, Remington's Pharmaceutical Sciences. Edited by Gennaro AR, 19th ed. Pennsylvania: Mack Publishing Company, 1995), and includes, but is not limited to: pH regulator, surfactant, adjuvant, ionic strength enhancer. For example, the pH adjusting agent includes, but is not limited to, phosphate buffer; the surfactant includes, but is not limited to, cationic, anionic or nonionic surfactant, such as Tween-80; and the ionic strength enhancer includes, but is not limited to, sodium chloride.

As used herein, the term "adjuvant" refers to a non-specific immune enhancer, which can enhance the body's immune response to an antigen or change the type of immune response when it is delivered into the body in advance or together with the antigen. There are many adjuvants, including but not limited to aluminum adjuvant (e.g., aluminum hydroxide), Freund's adjuvant (e.g., complete Freund's adjuvant and incomplete Freund's adjuvant), *Corynebacterium parvum*, lipopolysaccharide, cytokine, etc. Freund's adjuvant is currently the most commonly used adjuvant in animal experiments. Aluminum hydroxide adjuvant is used more in clinical trials.

As used herein, the term "effective amount" refers to an amount sufficient to obtain or at least partially obtain the desired effect. For example, an effective amount for preventing a disease (e.g., RSV infection or a diseases associated with the RSV infection) refers to an amount sufficient to prevent, stop or delay the occurrence of a disease (e.g., RSV infection or a disease associated with the RSV infection); an effective amount for treating a disease refers to an amount sufficient to cure or at least partially prevent the disease and its complications in a patient who has already suffered from the disease. It is completely within the ability of those skilled in the art to determine such an effective amount. For example, the effective amount for therapeutic use will depend on the severity of disease to be treated, the overall state of the patient's own immune system, the patient's general conditions such as age, weight and gender, the manner of administrating drug, and other treatments administered simultaneously and the like.

As used herein, the term "subject" refers to a mammal, such as a primate, such as a human.

As used herein, the term "about", when referring to a measurable value (e.g., concentration of substance, time, temperature, and the like), is meant to encompass the range of ±10%, ±5% or ±1% of a given value. In certain exemplary embodiments, the term "about" refers to the range between plus and minus 10% of a given value; for example, about 0.015% refers to a range of 0.0135% to 0.0165%.

After a large number of experimental studies, the inventors unexpectedly found that: when fixing/inactivating a RSV, by using a specific fixing agent (e.g., formaldehyde, or paraformaldehyde), and using a specific fixation/inactivation condition (e.g., specific concentration of fixing agent), a particularly advantageous inactivated RSV could be obtained, which comprised a higher content of pre-F protein (i.e., in the inactivated RSV obtained in the present invention, more F protein existed in pre-F conformation) in comparison with the inactivated virus obtained by conventional methods. Meanwhile, when the RSV was preserved, by using a specific storage condition (e.g., a specific storage solution ion concentration), the pre-F protein in the RSV could be maintained and stabilized, and the content of the pre-F protein could even be maintained at a level close to that of a fresh live virus. This is particularly advantageous because such inactivated RSV will present more strong neutralizing epitopes that only exist in the pre-F protein but not in the post-F protein, thereby inducing the body to produce stronger neutralizing activity against RSV, so that it is particularly suitable for the development of vaccines against RSV for preventing or treating RSV infection or a disease associated with the RSV infection (e.g., pneumonia, such as pediatric pneumonia).

Therefore, in the first aspect, the present invention provides a method for inactivating an isolated respiratory syncytial virus (RSV) and stabilizing a pre-F protein in the RSV, which comprises the following steps:

(1) providing an isolated live RSV;

(2) fixing and inactivating the live RSV by using a fixing agent selected from the group consisting of: a formaldehyde solution having a formaldehyde concentration of about 0.015% to about 0.27% by weight (w/w, the same hereinafter) and a paraformaldehyde solution having a paraformaldehyde concentration of about 0.02% to about 0.3% by weight (w/w, the same hereinafter);

(3) removing the fixing agent from the product of step (2), thereby obtaining an inactivated RSV.

In the present invention, the expression "isolated" refers to that the RSV is not contained in a cell (e.g., a host cell) or not provided in a cell (e.g., a host cell) in any other ways.

In certain preferred embodiments, in step (2), the fixing agent is a formaldehyde solution and has a formaldehyde concentration of about 0.015% to about 0.27%, for example, about 0.0156% to about 0.2667%; for example, about 0.0156% to about 0.0234%, about 0.0234% to about 0.0244%, about 0.0244% to about 0.0351%, about 0.0351% to about 0.0527%, about 0.0527% to about 0.079%, about 0.079% to about 0.0977%, about 0.0977% to about 0.1185%, or about 0.1185% to about 0.1778%, or about 0.1778% to about 0.2667%. In some preferred embodiments, the formaldehyde solution is a solution of formaldehyde dissolved in an inorganic solvent. Preferably, the inorganic solvent is selected from the group consisting of water, medium and buffer. In certain exemplary embodiments, the buffer is phosphate buffered saline (PBS).

In certain preferred embodiments, the live RSV is fixed and inactivated by using a formaldehyde solution at a temperature of about 0° C. to about 40° C. (e.g., about 0° C. to about 4° C., about 4° C. to about 10° C., about 10° C. to about 15° C., about 15° C. to about 20° C., about 20° C. to about 25° C., about 25° C. to about 30° C., about 30° C. to about 35° C., about 35° C. to about 37° C., or about 37° C. to about 40° C.; for example, about 4° C., about 25° C. or about 37° C.).

In certain preferred embodiments, the live RSV is fixed and inactivated by using a formaldehyde solution for a duration of about 6 h to about 36 h (e.g., about 6 h to about 12 h, about 12 h to about 24 h, or about 24 h to about 36 h; for example, about 6 h, about 12 h, about 24 h, or about 36 h). In certain preferred embodiments, the live RSV is fixed and inactivated by using a formaldehyde solution for a duration of about 12 hours.

In certain preferred embodiments, in step (2), the fixing agent is a paraformaldehyde solution, and has a paraformaldehyde concentration of about 0.02% to about 0.3%, for example, about 0.026% to about 0.2963%; for example, about 0.026% to about 0.039%, about 0.039% to about 0.0585%, about 0.0585% to about 0.0625%, about 0.0625% to about 0.0878%, about 0.0878% to about 0.1317%, about 0.1317% to about 0.1975%, about 0.1975% to about 0.25%, or about 0.25% to about 0.2963%. In some preferred embodiments, the paraformaldehyde solution is a solution of paraformaldehyde dissolved in an inorganic solvent. Preferably, the inorganic solvent is selected from the group consisting of water, medium and buffer. In certain exemplary embodiments, the buffer is phosphate buffered saline (PBS).

In certain preferred embodiments, the live RSV is fixed and inactivated by using a paraformaldehyde solution at a temperature of about 10° C. to about 40° C. (e.g., about 10° C. to about 15° C., about 15° C. to about 20° C., about 20° C. to about 25° C., about 25° C. to about 30° C., about 30° C. to about 35° C., about 35° C. to about 37° C., or about 37° C. to about 40° C.; for example, about 10° C., about 25° C., about 37° C. or about 40° C.).

In certain preferred embodiments, the live RSV is fixed and inactivated by using a paraformaldehyde solution for a duration of about 6 h to about 36 h (e.g., about 6 h to about 12 h, about 12 h to about 24 h, or about 24 h to about 36 h; for example, about 6 h, about 12 h, about 24 h, or about 36 h). In certain preferred embodiments, the live RSV is fixed and inactivated by using a paraformaldehyde solution for a duration of about 12 hours.

In certain preferred embodiments, the live RSV is fixed and inactivated by using a paraformaldehyde solution with a concentration of about 0.015% to about 0.25% (e.g., about 0.0156% to about 0.25%; for example, about 0.0156% to about 0.0625%, or about 0.0625% to about 0.25%) at a temperature of about 20° C. to about 30° C. (e.g., about 20° C., about 25° C., or about 30° C.) for a duration of about 6 h to about 36 h (e.g., about 6 h to about 12 h, about 12 h to about 24 h, or about 24 h to about 36 h; for example, about 12 h).

In certain preferred embodiments, the live RSV is fixed and inactivated by using a paraformaldehyde solution with a concentration of about 0.0156% to about 0.0625% at a temperature of about 35° C. to about 40° C. (e.g., about 35° C., about 37° C., or about 40° C.) for a duration of about 6 h to about 36 h (e.g., about 6 h to about 12 h, about 12 h to about 24 h, or about 24 h to about 36 h; for example, about 12 h).

In some preferred embodiments, in step (1), the isolated live RSV is provided by the following steps: (1a) infecting a host cell with a RSV; (1b) culturing the infected host cell obtained in step (1a) under a condition that allows the propagation of the RSV; and (1c) collecting and lysing the cultured host cell obtained in step (1b), and recovering the RSV from lysate thereof. In the present invention, the product of step (1c) does not comprise the host cell.

In certain preferred embodiments, in step (1c), the RSV is recovered by centrifugation or filtration, and the host cell is removed.

In certain preferred embodiments, the host cell is an adherent cell. In certain preferred embodiments, the host cell is a suspension cell. In certain preferred embodiments, the host cell is a primary cell. In certain preferred embodiments, the host cell is an established cell line. In certain preferred embodiments, the host cell is selected from the group consisting of respiratory epithelial cell, liver cell, lung cell, kidney cell, cervical cell, ovarian cell, bone cell, breast cell, striated muscle cell, gastric epithelial cell, skin epidermal cell, fibroblast and prostate cell of a mammal (e.g., rodent and primate, such as mouse, monkey, and human); such as Hep-2 cell, CNE1 cell, CNE2 cell, BEL-7404 cell, BEL-7402 cell, QSG-7701 cell, PLC/PRF/5 cell, Huh7 cell, Huh7.5.1 cell, SSMC-7721 cell, BNL-HCC cell, Hep3B, SNU-739 cell, TIB75 cell, A549 cell, H480 cell, H1299 cell, H441 cell, H368 cell, H1335 cell, H23 cell, L929 cell, 293FT cell, 293T cell, 293β5 cell, Vero cell, BHK-MKL cell, RK-13 cell, HeLa cell, TZM-bl cell, SK-OV-3 cell, U2-OS cell, 143B cell, MCF-7 cell, MDA-MB-231 cell, T-47D cell, RD cell, BGC-823 cell, AGS cell, A431NS cell, MeWo cell, LNCap cell, RM1 cell and PC-3 cell. In certain preferred embodiments, in step (1c), the cultured host cell is collected by scraping with a spatula or by digestion with trypsin or by filtration or centrifugation. In certain preferred embodiments, in step (1c), the cultured host cell is lysed by an ultrasonic method.

In some preferred embodiments, in step (3), the fixing agent is removed by dialysis, filtration or centrifugation. In some preferred embodiments, in step (3), the product of step (2) is dialyzed against a solution comprising no fixing agent to remove the fixing agent.

In some preferred embodiments, in step (3), the product of step (2) is dialyzed against a salt solution to remove the fixing agent. In certain preferred embodiments, the salt solution has an ion concentration of about 100 to about 1000 mM (e.g., about 150 to about 1000 mM, for example, about 100 to about 150 mM, about 150 to about 200 mM, about 200 to about 250 mM, about 250 to about 300 mM, about 300 to about 350 mM, about 350 to about 400 mM, about 400 to about 450 mM, about 450 to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, about 850 to about 900 mM, about 900 to about 950 mM, about 950 to about 1000 mM, for example, about 150 mM, about 330 mM, about 550 mM, about 880 mM).

In some preferred embodiments, in step (3), the product of step (2) is dialyzed against a salt solution with an ion concentration of about 300 to about 1000 mM (e.g., about 300 to about 900 mM, about 300 to about 350 mM, about 350 to about 400 mM, about 400 to about 450 mM, about 450 to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, or about 850 to about 900 mM; for example, about 330 mM, about 550 mM or about 880 mM).

In certain exemplary embodiments, the salt solution comprises sodium salt (e.g., sodium chloride, disodium hydrogen phosphate or a combination thereof) and/or potassium salt (e.g., potassium chloride, potassium dihydrogen phosphate or a combination thereof)). In certain exemplary embodiments, the salt solution is phosphate buffered saline (PBS). In certain exemplary embodiments, the salt solution is a sodium salt solution (e.g., sodium chloride, disodium hydrogen phosphate, or a combination thereof).

In certain preferred embodiments, the retained pre-F protein in the inactivated RSV obtained by the method of the present invention can be at least 40%, at least 45%, at least 50%, at least 55%, at least 60%, at least 65%, at least 70%, at least 75%, at least 80%, at least 85%, at least 90%, at least 95%, or 100%, compared with the pre-F protein in a freshly harvested live virus. In certain preferred embodiments, the retained pre-F protein in the inactivated RSV obtained by the method of the present invention can be at least 40%, at least 45%, at least 50%, at least 55%, at least 60%, at least 65%, at least 70%, at least 75%, at least 80%, at least 85%, at least 90%, at least 95%, or 100%, compared with the pre-F protein in a freshly harvested live virus, and the above ratio can be maintained for at least 24 h, for example at least 48 h, or at least 72 h.

In certain preferred embodiments, the pre-F protein in the inactivated RSV can maintain its conformation for at least 24 hours, such as at least 48 hours, or at least 72 hours.

In a second aspect, the present invention provides a method for preserving a RSV and stabilizing a pre-F protein in the RSV, which comprises a step of placing the RSV in a storage solution, wherein the storage solution is a salt solution having an ion concentration of about 150 to about 1000 mM (e.g., about 200 to about 1000 mM, or about 300 to about 1000 mM; for example, about 150 to about 200 mM, about 200 to about 250 mM, about 250 to about 300 mM, about 300 to about 350 mM, about 350 to about 400 mM, about 400 to about 450 mM, about 450 to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, about 850 to about 900 mM, about 900 to about 950 mM, about 950 to about 1000 mM, for example about 150 mM, about 330 mM, about 550 mM, or about 880 mM).

In some preferred embodiments, the storage solution is a salt solution having an ion concentration of about 300 to about 1000 mM (e.g., about 300 to about 900 mM, about 300 to about 350 mM, about 350 to about 400 mM, about 400 to about 450 mM, about 450 mM to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, or about 850 to about 900 mM; for example about 330 mM, about 550 mM or about 880 mM).

In some preferred embodiments, the storage solution comprises sodium salt (e.g., sodium chloride, disodium hydrogen phosphate or a combination thereof) and/or potassium salt (e.g., potassium chloride, potassium dihydrogen phosphate or a combination thereof). In certain exemplary embodiments, the storage solution is phosphate buffered saline (PBS), or the storage solution is a sodium salt solution (e.g., sodium chloride, disodium hydrogen phosphate, or a combination thereof).

In certain preferred embodiments, the inactivated RSV is placed in a storage solution by dialysis, filtration or centrifugation.

In certain preferred embodiments, the RSV is dialyzed against a salt solution, so that the RSV is placed in a storage solution; wherein the salt solution has an ion concentration of about 150 to about 1000 mM (e.g., about 200 to about 1000 mM, or about 300 to about 1000 mM; for example, about 150 to about 200 mM, about 200 to about 250 mM, about 250 to about 300 mM, about 300 to about 350 mM, about 350 to about 400 mM, about 400 to about 450 mM, about 450 to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, about 850 to about 900 mM, about 900 to about 950 mM, about 950 to about 1000 mM, for example about 150 mM, about 330 mM, about 550 mM, or about 880 mM).

In certain preferred embodiments, the salt solution has an ion concentration of about 300 to about 1000 mM (e.g., about 300 to about 900 mM, about 300 to about 350 mM, about 350 to about 400 mM, about 400 to about 450 mM, about 450 mM to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, or about 850 to about 900 mM; for example, about 330 mM, about 550 mM, or about 880 mM).

In certain preferred embodiments, the salt solution comprises sodium salt (e.g., sodium chloride, disodium hydrogen phosphate or a combination thereof) and/or potassium salt (e.g., potassium chloride, potassium dihydrogen phosphate or a combination thereof); for example, the salt solution is phosphate buffered saline (PBS), or the salt solution is a sodium salt solution (e.g., sodium chloride, disodium hydrogen phosphate or a combination thereof).

In certain preferred embodiments, the RSV is dialyzed against a salt solution for a duration of about 6 h to about 24 h (e.g., about 12 h to about 24 h, about 12 h to about 20 h, or about 16 h to about 20 h; for example, about 18 h).

In certain preferred embodiments, the RSV is a live virus. In such embodiments, the method is used to preserve a live RSV and stabilize a pre-F protein in the live RSV. In certain preferred embodiments, the RSV is a live virus freshly harvested from a host cell.

In certain preferred embodiments, the RSV is an inactivated virus. In such embodiments, the method is used to preserve an inactivated RSV and stabilize a pre-F protein in the inactivated RSV. In the present invention, the method for inactivating a virus to destroy its ability to infect a cell of a subject (e.g., mammal, such as human) is well known to those skilled in the art, including chemical methods and physical methods. Suitable methods for inactivating virus include, but are not limited to, treatment with an effective amount of one or more items selected from the group consisting of: fixing agent (e.g., alcohol (e.g., methanol), aldehyde (e.g., formaldehyde, glutaraldehyde), β-propiolactone, phenol, etc.), heat, radiation (e.g., electromagnetic radiation, X-ray radiation, γ-radiation, ultraviolet radiation, etc.), psoralen, methylene blue, ozone, etc.

In certain preferred embodiments, the inactivated RSV is provided by the following steps:

(i) providing an isolated live RSV;
  (ii) fixing and inactivating the live RSV by using a fixing agent;
  (iii) removing the fixing agent from the product of step (ii), thereby obtaining an inactivated RSV.

In some preferred embodiments, in step (ii), the fixing agent is selected from the group consisting of formaldehyde solution, paraformaldehyde solution, glutaraldehyde solution and β-propiolactone solution. In certain preferred embodiments, the fixing agent is a formaldehyde solution or a paraformaldehyde solution.

In certain preferred embodiments, the inactivated RSV is provided by the method of inactivating a RSV as described in the first aspect.

In some preferred embodiments, the method comprises the following steps:

(1) providing an isolated live RSV;
  (2) fixing and inactivating the live RSV by using a fixing agent;
  (3) dialyzing the product of step (2) against a salt solution to obtain a storage solution containing the inactivated RSV;
  wherein in step (3), the salt solution has an ion concentration of about 150 to about 1000 mM (e.g., about 200 to about 1000 mM, or about 300 to about 1000 mM; for example, about 150 to about 200 mM, about 200 to about 250 mM, about 250 to about 300 mM, about 300 to about 350 mM, about 350 to about 400 mM, about 400 to about 450 mM, about 450 to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, about 850 to about 900 mM, about 900 to about 950 mM, about 950 to about 1000 mM, for example, about 150 mM, about 330 mM, about 550 mM, or about 880 mM).

In certain preferred embodiments, the salt solution has an ion concentration of about 300 to about 1000 mM (e.g., about 300 to about 900 mM, about 300 to about 350 mM, about 350 to about 400 mM, about 400 to about 450 mM, about 450 mM to about 500 mM, about 500 to about 550 mM, about 550 to about 600 mM, about 600 to about 650 mM, about 650 to about 700 mM, about 700 to about 750 mM, about 750 to about 800 mM, about 800 to about 850 mM, or about 850 to about 900 mM; for example, about 330 mM, about 550 mM, or about 880 mM).

In some preferred embodiments, the storage solution comprises sodium salt (e.g., sodium chloride, disodium hydrogen phosphate or a combination thereof) and/or potassium salt (e.g., potassium chloride, potassium dihydrogen phosphate or a combination thereof); for example, the storage solution is phosphate buffered saline (PBS), or the storage solution is a sodium salt solution (e.g., sodium chloride, disodium hydrogen phosphate or a combination thereof).

In some preferred embodiments, in step (2), the fixing agent is a formaldehyde solution.

In certain preferred embodiments, the concentration of formaldehyde is not greater than about 0.27% by weight, such as not greater than about 0.2667%. In certain preferred embodiments, the live RSV is fixed and inactivated by using a formaldehyde solution at a temperature of about 0° C. to about 40° C. (e.g., about 0° C. to about 4° C., about 4° C. to about 10° C., about 10° C. to about 15° C., about 15° C. to about 20° C., about 20° C. to about 25° C., about 25° C. to about 30° C., about 30° C. to about 35° C., about 35° C. to about 37° C., or about 37° C. to about 40° C.; for example, about 4° C., about 25° C. or about 37° C.). In certain preferred embodiments, the live RSV is fixed and inactivated by using a formaldehyde solution for a duration of about 6 h to about 36 h (e.g., about 6 h to about 12 h, about 12 h to about 24 h, or about 24 h to about 36 h; for example, about 6 h, about 12 h, about 24 h, or about 36 h).

In some preferred embodiments, in step (2), the fixing agent is a paraformaldehyde solution.

In certain preferred embodiments, the concentration of paraformaldehyde is not greater than about 0.3% by weight, for example, not greater than about 0.2963%. In certain preferred embodiments, the live RSV is fixed and inactivated by using a formaldehyde solution at a temperature of about 10° C. to about 40° C. (e.g., about 10° C. to about 15° C., about 15° C. to about 20° C., about 20° C. to about 25° C., about 25° C. to about 30° C., about 30° C. to about 35° C., about 35° C. to about 37° C., or about 37° C. to about 40° C.; for example, about 10° C., about 25° C., about 37° C. or about 40° C.). In certain preferred embodiments, the live RSV is fixed and inactivated by using a paraformaldehyde solution for a duration of about 6 h to about 36 h (e.g., about 6 h to about 12 h, about 12 h to about 24 h, or about 24 h to about 36 h; for example, about 6 h, about 12 h, about 24 h, or about 36 h).

In certain preferred embodiments, the method further comprises a step of preserving a storage solution comprising the RSV at a temperature of about 0° C. to about 40° C. (e.g., about 0° C. to about 4° C., about 4° C. to about 10° C., about 10° C. to about 15° C., about 15° C. to about 20° C., about 20° C. to about 25° C., about 25° C. to about 30° C., about 30° C. to about 35° C., about 35° C. to about 37° C., or about 37° C. to about 40° C.; for example, about 4° C., about 25° C. or about 37° C.).

In certain preferred embodiments, the retained pre-F protein in the inactivated RSV preserved by the method of the present invention can be at least 60% (e.g., at least 65%, at least 70%, at least 75%, at least 80%, at least 85%, at least 90%, at least 95%, or 100%) compared with the pre-F protein in a freshly harvested live virus. In certain preferred embodiments, the retained pre-F protein in the inactivated RSV preserved by the method of the present invention can be at least 60% (e.g., at least 65%, at least 70%, at least 75%, at least 80%, at least 85%, at least 90%, at least 95%, or 100%) compared with the pre-F protein in a freshly harvested live virus, and the above ratio can be maintained for at least 24 h, such as at least 48 h, or at least 72 h.

In another aspect, the present invention provides an inactivated RSV, which is prepared by the method as described in the first aspect and/or preserved by the method as described in the second aspect.

In another aspect, the present invention provides a vaccine, which comprises the inactivated RSV according to the present invention, and optionally, a pharmaceutically acceptable carrier and/or excipient (e.g., an adjuvant).

In certain preferred embodiments, the inactivated RSV is prepared by the method described in the first aspect; or, the inactivated RSV is preserved by the method described in the second aspect; or, the inactivated RSV is prepared by the method described in the first aspect and is preserved by the method described in the second aspect.

The vaccine of the present invention can be used to prevent, treat or suppress RSV infection or a disease associated with the RSV infection in a subject (e.g., pneumonia, such as pediatric pneumonia).

The vaccine of the present invention can be used alone or in combination with another pharmaceutically active agent (e.g., interferon drug, such as interferon or peginterferon).

In another aspect, the present invention provides a method for preparing a vaccine, which comprises mixing the inactivated RSV according to the present invention with a pharmaceutically acceptable carrier and/or excipient (e.g., an adjuvant).

In certain preferred embodiments, the inactivated RSV is prepared by the method described in the first aspect; or, the inactivated RSV is preserved by the method described in the second aspect; or, the inactivated RSV is prepared by the method described in the first aspect and is preserved by the method described in the second aspect.

In another aspect, the present invention provides a method for preventing, treating or inhibiting RSV infection or a disease associated with RSV infection (e.g., pneumonia, such as pediatric pneumonia) in a subject, which comprises administering the subject an effective amount of the inactivated RSV according to the present invention, or the vaccine according to the present invention.

In certain preferred embodiments, the inactivated RSV is prepared by the method described in the first aspect; or, the inactivated RSV is preserved by the method described in the second aspect; or, the inactivated RSV is prepared by the method described in the first aspect and is preserved by the method described in the second aspect.

In another aspect, there is provided a use of the inactivated RSV of the present invention in manufacture of a vaccine for preventing, treating or inhibiting RSV infection in a subject or a disease associated with the RSV infection (e.g., pneumonia, such as Pediatric pneumonia).

In certain preferred embodiments, the inactivated RSV is prepared by the method described in the first aspect; or, the inactivated RSV is preserved by the method described in the second aspect; or, the inactivated RSV is prepared by the method described in the first aspect and is preserved by the method described in the second aspect.

In another aspect, there is provided an inactivated RSV or vaccine of the present invention is provided, for use in preventing, treating or inhibiting RSV infection or a disease associated with RSV infection in a subject (e.g., pneumonia, such as pediatric pneumonia).

THE BENEFICIAL EFFECTS OF THE PRESENT INVENTION

As compared with the prior art, the technical solution of the present invention has the following beneficial effects:

(1) The method of inactivating RSV according to the present invention can be used to prepare an inactivated RSV comprising pre-F protein, and maintain and stabilize the conformation of pre-F protein.

(2) The method of preserving RSV according to the present invention can maintain and stabilize the conformation of pre-F protein, and even maintain the content of pre-F protein at a level close to that of a fresh live virus, and can also be used to prepare an inactivated RSV containing pre-F protein.

(3) As compared with an inactivated virus obtained by a conventional inactivation or preservation method, the inactivated RSV according to the present invention comprises a higher content of pre-F protein and can induce more effective immune response in a body, so that it is particularly suitable for the development of a vaccine against RSV to prevent or treat RSV infection or a disease associated with the RSV infection (e.g., pneumonia, such as pediatric pneumonia).

The embodiments of the present invention will be described in detail below with reference to the accompanying drawings and examples. However, those skilled in the art will understand that the following drawings and examples are only used to illustrate the present invention, and not to limit the scope of the present invention. Various objects and advantageous aspects of the present invention will become apparent to those skilled in the art based on the accompanying drawings and the following detailed description of the preferred embodiments.

SEQUENCE DESCRIPTION

Figure 1:
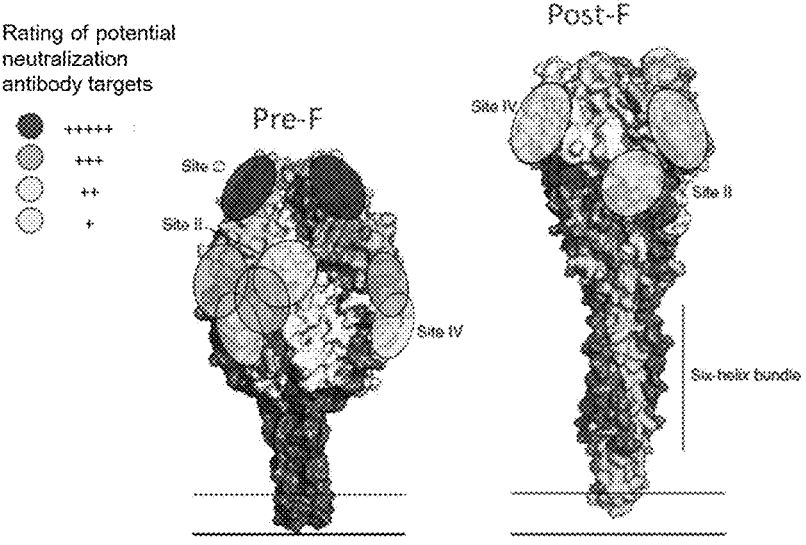
FIG. 1 shows the distribution of neutralizing epitopes on pre-F and post-F proteins. The results show that pre-F and post-F proteins share about 50% of the protein surface, and epitopes with high neutralizing activity (strong neutralizing epitopes) such as site φ are mainly distributed in the pre-F conformation, while post-F conformation mainly comprises epitopes with weaker neutralizing activity (weak neutralizing epitopes), such as site II and site IV.

The information of the sequence involved in the present application is as follows:

```
(amino acid sequence of F protein)
                                   SEQ ID NO: 1
MELLILKANAITTILTAVTFCFASGQNITEEFYQSTCSAVSKGYLSALR

TGWYTSVITIELSNIKENKCNGTDAKVKLIKQELDKYKNAVTELQLLMQ

STPPTNNRARRELPRFMNYTLNNAKKTNVTLSKKRKRRFLGFLLGVGSA

IASGVAVSKVLHLEGEVNKIKSALLSTNKAVVSLSNGVSVLTSKVLDLK

NYIDKQLLPIVNKQSCSISNIETVIEFQQKNNRLLEITREFSVNAGVTT

PVSTYMLTNSELLSLINDMPITNDQKKLMSNNVQIVRQQSYSIMSIIKE

EVLAYVVQLPLYGVIDTPCWKLHTSPLCTTNTKEGSNICLTRTDRGWYC
```

-continued

```
DNAGSVSFFPQAETCKVQSNRVFCDTMNSLTLPSEINLCNVDIFNPKYD

CKIMTSKTDVSSSVITSLGAIVSCYGKTKCTASNKNRGIIKTFSNGCDY

VSNKGMDTVSVGNTLYYVNKQEGKSLYVKGEPIINFYDPLVFPSDEFDA

SISQVNEKINQSLAFIRKSDELLHNVNAGKSTTNIMITTIIIVIIVILL

SLIAVGLLLYCKARSTPVTLSKDQLSGINNIAFSN
```

EXAMPLES

The present invention will now be described with reference to the following examples which are intended to illustrate the present invention rather than limit the present invention.

Unless otherwise specified, the molecular biology experimental methods and immunoassay methods used in the present invention basically refer to the methods described by J. Sambrook et al., Molecular Cloning: Laboratory Manual, 2nd Edition, Cold Spring Harbor Laboratory Press, 1989, and FM Ausubel et al., Short Molecular Biology Experiment Guide, 3rd Edition, John Wiley & Sons, Inc., 1995; the restriction enzymes were used in accordance with the conditions recommended by the product manufacturers. Those skilled in the art know that the examples describe the present invention by way of example and are not intended to limit the scope of protection sought to be protected by the present invention.

Example 1. Inactivation of RSV

1. Materials and Instruments

Hep-2 cells (ATCC® CCL-23™), Vero cells (ATCC): obtained from ATCC.

hRSV (pSynkRSV A2 D46F): standard strain of human respiratory syncytial virus, obtained from NIH of the National Institutes of Health of the USA.

5C4 antibody: prepared in-house. The 5C4 antibody specifically recognizes and binds to pre-F protein, but does not recognize or bind to post-F protein. The 5C4 antibody recognizes Site φ epitope on the pre-F protein, and it is a strong neutralization antibody with a significantly higher neutralizing activity than Palivizumab. For detailed information about 5C4 antibody, please refer to Chinese Patent Application 201480013927.7 and PCT International Application PCT/CN2014/073505.

8C2 antibody: prepared in-house. The 8C2 antibody can specifically bind to both of pre-F protein and post-F protein. The 8C2 antibody recognizes Site II epitope on pre-F protein and post-F protein, and it is a neutralization antibody with a neutralizing activity basically equivalent to that of Palivizumab.

9F7 antibody: prepared in-house. The 9F7 antibody is an antibody that specifically recognizes hepatitis E virus, and cannot specifically react with either pre-F protein or post-F protein. For detailed information about the 9F7 antibody, see, for example, Min Zhao et al. J Biol Chem, 2015, 290: 19910-19922.

GaM-FITC: FITC-labeled goat anti-mouse antibody, obtained from Sigma.

Bio-Dot SF blotting device, obtained from Bio-Rad Company.

ChemiDoc MP full-wavelength gel-imaging system, obtained from Bio-Rad.

Large desktop high-speed refrigerated centrifuge (Model: Sorvall ST16R), obtained from Thermo Company.

2. Virus Preparation

Hep-2 cells (ATCC® CCL-23™) or Vero cells were inoculated in a cell culture plate, and cultured by using MEM medium (Gibco, article number: 11095072) containing 10% FBS (Gibco, catalog number: 10099141) and 100 U/ml penicillin-streptomycin (Gibco, catalog number: 15140122). When the cell density reached 80% to 90% confluence, the cells were infected with hRSV (pSynkRSV A2 D46F), MOI=0.3. After infection, the cells were cultured for 72 hours.

After the culture, the cells were collected with a cell scraper, cooled on ice, and then crushed/lysed with an ultrasonic cell disruptor to release viruses. The cell lysate was centrifuged and the supernatant was collected, and then the virus-containing supernatant was subpackaged into cryogenic vials, quickly frozen in a −80° C. refrigerator, and preserved for later use.

3. Fixation and Inactivation of Viruses

In each EP tube, a fixing solution of specified type and concentration (2×) was prepared by using 1×PBS. The viruses were thawed at 37° C., the virus solution was mixed with each fixing solution in a volume ratio of 1:1, and subjected to inactivation/fixation for a specified time at a specified temperature. The fixing agents used were as follows:

Formaldehyde (CH$_2$O, CP, Xilong Chemical, article number: 50-00-0);

Paraformaldehyde (HO(CH$_2$O)$_n$H, n=10-100, SIGMA-ALDRICH, article number: 16005);

Methanol (CH$_3$OH, Methanol, AR Xilong Chemical, catalog number: 1030003AR500);

Glutaraldehyde (Glutaraldehyde solution, Fluka, catalog number: 49629);

β-Propiolactone (Propiolactone, research grade, SERVA, catalog number: 57-57-8).

After fixation, dialysis was carried out in a salt solution of 150 mM or above (e.g., 330 mM, 550 mM, 880 mM) at 4° C. or 25° C. or 37° C. for 18 hours to remove residual fixing agent. After dialysis, the sample was taken out, placed in a 1.5 ml EP tube, and placed at 25° C. for 24 h or 48 h or 72 h.

4. Detection of Pre-F and Post-F Proteins on Surface of Inactivated Viruses

100 µl of the inactivated virus solution was taken from the above EP tube, and loaded on a nitrate cellulose membrane by using Bio-Dot SF blotting device. At room temperature, blocking was carried out by using 5% skimmed milk for 1 hour.

At room temperature, the nitrocellulose membrane was incubated with a primary antibody (diluted in 1×PBS) for 1 h, 20 ml per membrane. The primary antibody included: 5C4 antibody (2 ng/µl) that specifically bound to pre-F protein; 8C2 antibody (0.3 ng/µl) that bound to pre-F protein and post-F protein; and 9F7 antibody (0.3 ng/µl) that did not bind to pre-F protein and post-F protein. After incubation, washing was performed for 3 times with 1×PBS at 25° C., 10 min/time. Subsequently, the nitrocellulose membrane was incubated with secondary antibody GaM-FITC (Sigma, article number: F5387-2 mL; 1:3000 diluted in 1×PBS) for 1 h at room temperature in the dark. After incubation, washing was performed for 3 times with 1×PBS at 25° C., 10 min/time. Subsequently, ChemiDoc MP full-wavelength gel-imaging system of Bio-Rad was used for detection and photography, and the experimental data were recorded.

5. Data Processing

The above-mentioned detection and photographing data of nitrocellulose membrane were analyzed by Image Lab software. The specific operation was as follows: for each fixing solution-treated sample, after being incubated separately with three primary detection antibodies (5C4, 8C2, 9F7, respectively), three different bands were produced, and then three different FITC signal intensity values were produced, which were recorded as I-5C4, I-8C2, I-9F7, wherein I-9F7 was used as a negative control group. Wherein, the difference value obtained by subtracting I-9F7 from I-5C4 represented the relative amount of pre-F on viral surface under this fixation condition; and the difference value obtained by subtracting I-9F7 from I-8C2 represented the relative amount of total F protein on viral surface under this fixation condition.

In each group of experiments, a tube of untreated fresh virus sample was used as the control group, which was directly loaded onto nitrocellulose membrane, and subjected to subsequent detection same as the fixed samples, as shown in step 4. The ratio of the quantitative relative amount of pre-F in each experimental group sample divided by the relative amount of pre-F in the control group was used as the relative proportion of the fixed pre-F protein. The ratio of the quantitative relative amount of total F protein in each experimental group sample divided by the relative amount of total F protein in the control group was used as the relative proportion of the fixed total F protein.

Figure 2:
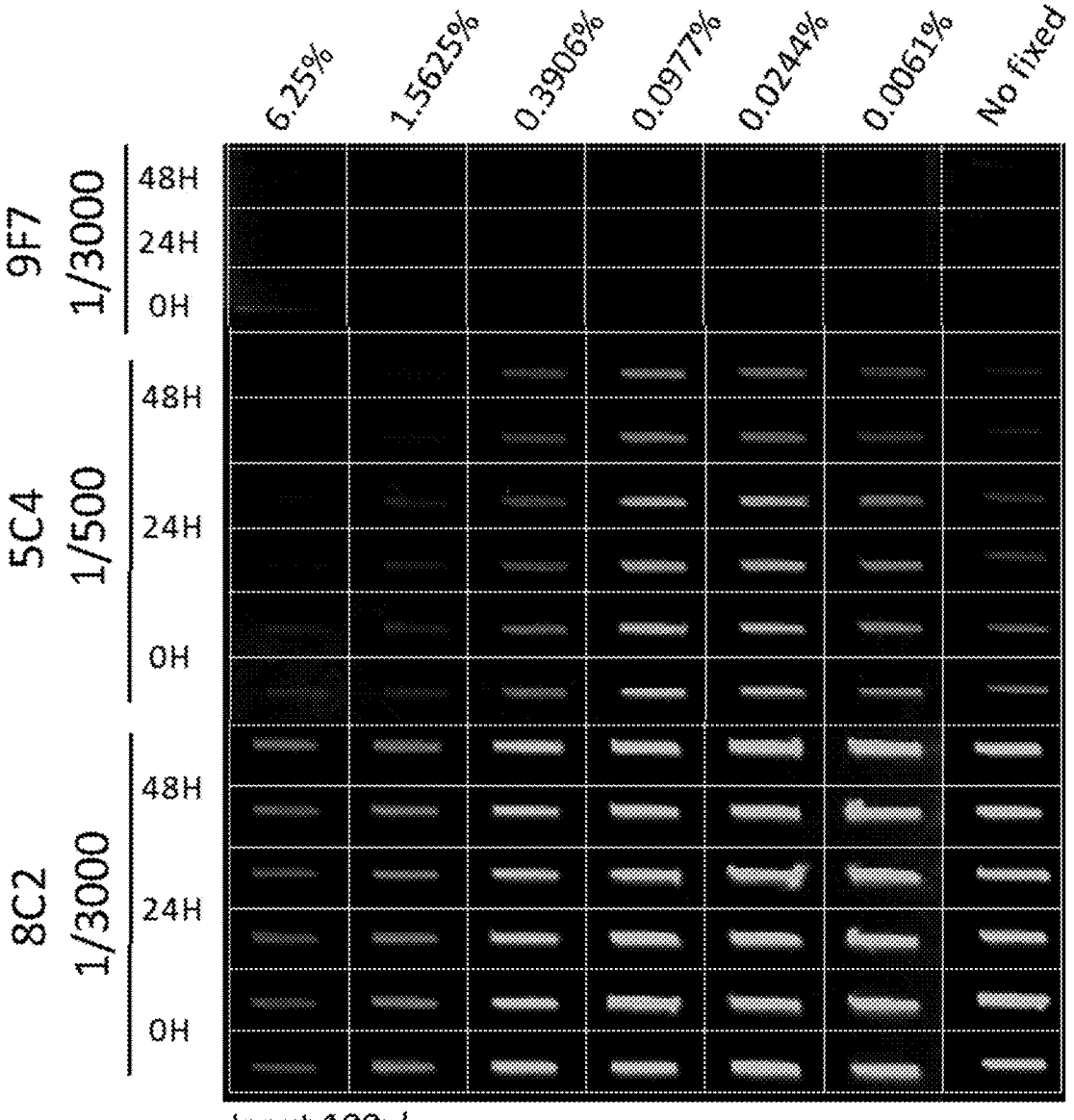
FIG. 2 shows gel-imaging images of samples incubated with 9F7 antibody, 5C4 antibody or 8C2 antibody, wherein the samples from left to right are: inactivated viruses obtained by using formaldehyde solution with concentrations of 6.25%, 1.5625%, 0.3906%, 0.0977%, 0.0244%, 0.0061% as fixing agent, as well as viruses that have not been fixed/inactivated with a fixing agent.

FIG. 2 shows gel-imaging images of samples incubated with 9F7 antibody, 5C4 antibody or 8C2 antibody, wherein the samples from left to right are: inactivated viruses obtained by using formaldehyde solution with concentrations of 6.25%, 1.5625%, 0.3906%, 0.0977%, 0.0244%, 0.0061% as fixing agent, as well as viruses that are fixed/inactivated without adding a fixing agent.

6. Experimental Results 6.1 Selection of Fixing Agent and Concentration Thereof

We first evaluated the stabilizing effects of fixing agents commonly used in this field on viral surface pre-F of RSV. For these fixing agents, we used the fixation conditions (i.e., temperature) recommended in the pharmacopoeia or references.

Figure 3:
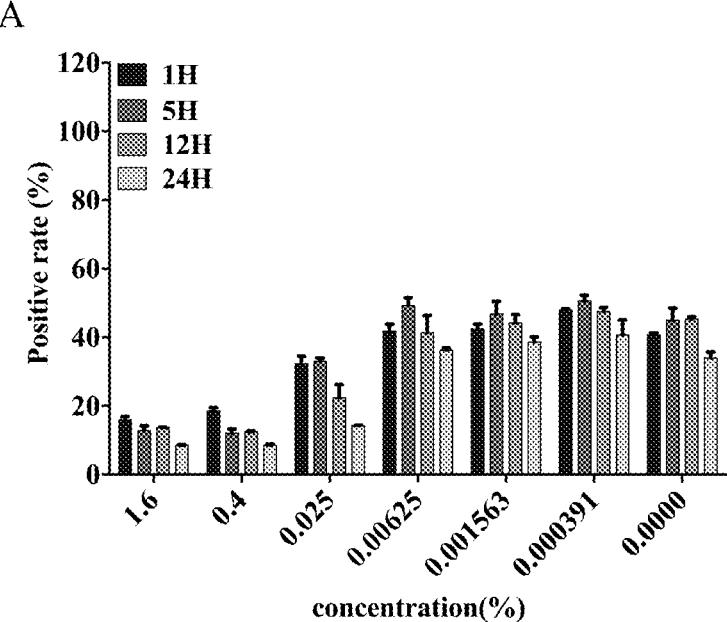
FIG. 3 shows the relative proportions of retained pre-F protein (FIG. 3A, incubation with 5C4 antibody) and the relative proportions of retained total F protein (pre-F conformation and/or post-F conformation) (FIG. 3B, incubation with 8C2 antibody) on viral surface in the samples treated with β-propiolactone of specified concentrations for specified time periods.
Figure 3:
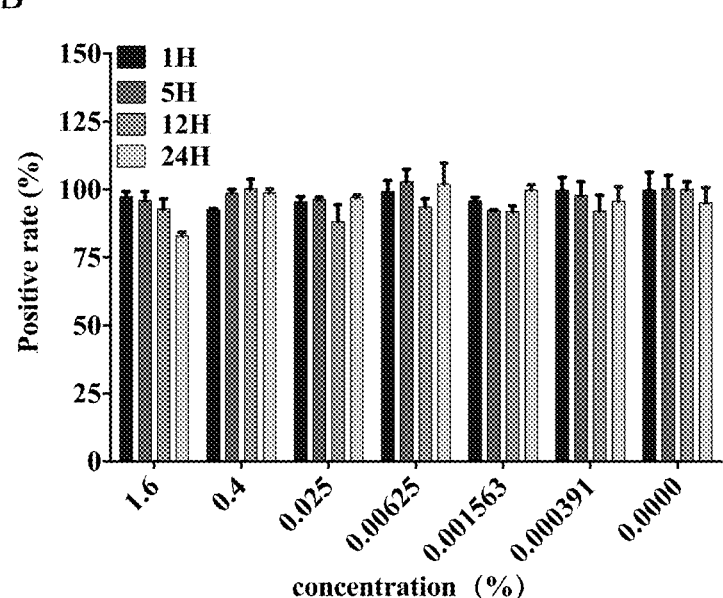

In short, β-propiolactone was formulated with 1×PBS to obtain a concentration of 2 times the specified concentration (1.6%, 0.4%, 0.025%, 0.00625%, 0.001563%, or 0.000391%), and allowed to stand at 25° C. for 30 min. Subsequently, at 25° C., the formulated β-propiolactone solution and RSV were uniformly mixed at a volume ratio of 1:1 for a specified time (1 h, 5 h, 12 h or 24 h). Concentration of 0% (that was, the non-fixed group) represented that the RSV sample and PBS were uniformly mixed at a volume ratio of 1:1 and incubated for a specified time (the same below). Subsequently, as described above, the fixing agent was removed by dialysis against 1×PBS, and the fixed sample was used for Dot blot detection. FIG. 3 shows the relative proportions of retained pre-F protein (FIG. 3A, incubation with 5C4 antibody) and the relative proportions of retained total F protein (pre-F conformation and/or post-F conformation) (FIG. 3B, incubation with 8C2 antibody) on viral surface in the samples treated with β-propiolactone of specified concentrations for specified time periods. The results showed that after the samples were treated for 1 h, 5 h, 12 h or 24 h with β-propiolactone of specified concentrations, they did not stably maintain the pre-F protein on viral surface as compared to the non-fixed group (0%). This result indicates that there is not an obvious preferred concentration of β-propiolactone to stabilize or maintain the conformation of pre-F protein on viral surface, so that it is not suitable for inactivating RSV.

Figure 4:
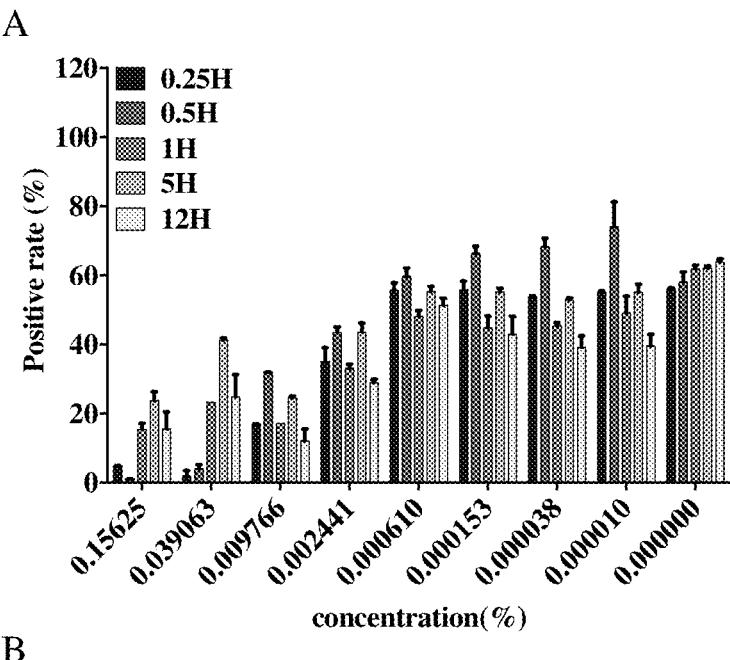
FIG. 4 shows the relative proportions of retained pre-F protein (FIG. 4A, incubation with 5C4 antibody) and the relative proportions of retained total F protein (pre-F conformation and/or post-F conformation) (FIG. 4B, incubation with 8C2 antibody) on viral surface in the samples treated with glutaraldehyde of specified concentrations for specified time periods.
Figure 4:
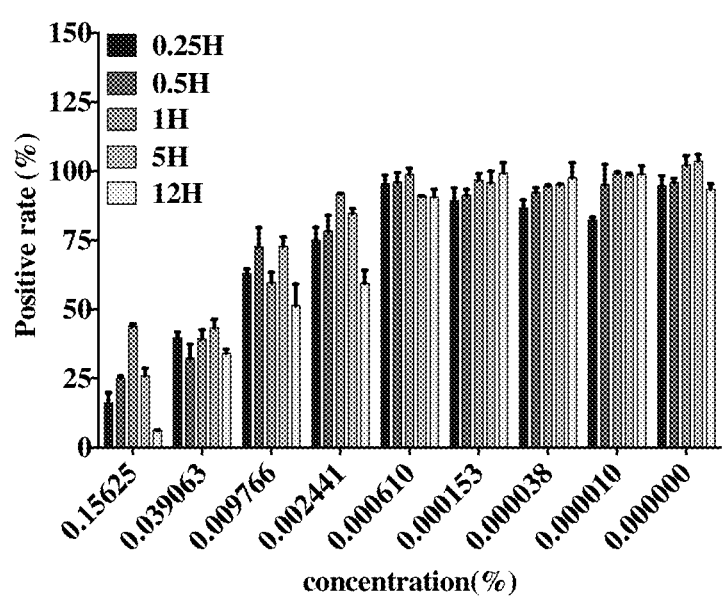

Glutaraldehyde was formulated with 1×PBS to obtain a concentration of 2 times the specified concentration (0.15625%, 0.039063%, 0.009766%, 0.002441%, 0.00061%, 0.000153%, 0.000038%, or 0.00001%), and allowed to stand at 25° C. for 30 min. Subsequently, at 25° C., the formulated glutaraldehyde solution and RSV were uniformly mixed at a volume ratio of 1:1 for a specified time (0.25 h, 0.5 h, 1 h, 5 h or 12 h). Subsequently, as described above, the fixing agent was removed by dialysis against 1×PBS, and the fixed sample was used for Dot blot detection. FIG. 4 shows the relative proportions of retained pre-F protein (FIG. 4A, incubation with 5C4 antibody) and the relative proportions of retained total F protein (pre-F conformation and/or post-F conformation) (FIG. 4B, incubation with 8C2 antibody) on viral surface in the samples treated with glutaraldehyde of specified concentrations for specified time periods. The results showed that after the samples were treated for 0.25 h, 0.5 h, 1 h, 5 h or 12 h with glutaraldehyde of specified concentrations, the pre-F protein on viral surface was not stably maintained as compared to the non-fixed group (0%). This result indicates that there is not a preferred concentration of glutaraldehyde to stabilize or maintain the conformation of pre-F protein on viral surface, so that it is not suitable for inactivating RSV.

Figure 5:
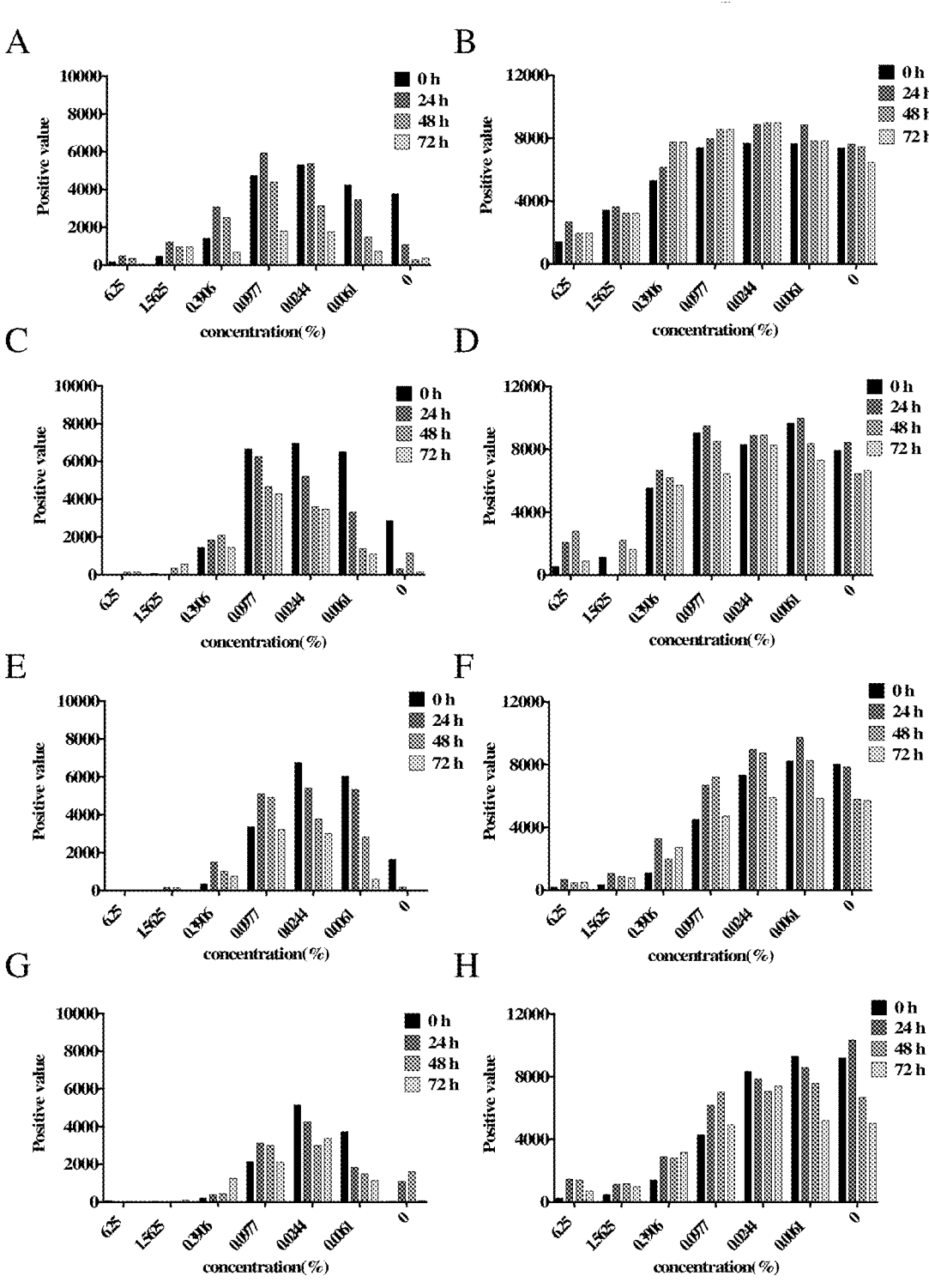
FIG. 5 shows the relative proportions of retained pre-F protein (FIGS. 5A, 5C, 5E, 5G, incubation with 5C4 antibody) and the relative proportions of retained total F protein (pre-F conformation and/or post-F conformation) (FIGS. 5B, 5D, 5F, 5H, incubation with 8C2 antibody) on viral surface in the samples treated with formaldehyde of specified concentrations for specified time periods.

Formaldehyde was formulated with 1×PBS to obtain a concentration of 2 times the specified concentration (6.25%, 1.5625%, 0.3906%, 0.0977%, 0.0244%, 0.0061%, 0%), and allowed to stand at 25° C. for 30 min. Subsequently, at 25° C., the formulated formaldehyde solution and RSV were uniformly mixed at a volume ratio of 1:1, and this was carried out for 6 h (FIGS. 5A-B), 12 h (FIG. 5C-D), 24 h (FIG. 5E-F), 36 h (FIG. 5G-H), respectively. Subsequently, as described above, the fixing agent was removed by dialysis against 1×PBS, and finally the inactivated virus was allowed to stand at 25° C. for a specified time (0 h, 24 h, 48 h, 72 h), and samples were taken at each time point for Dot Blot detection. FIG. 5 shows the relative proportions of retained pre-F protein (FIGS. 5A, 5C, 5E, 5G, incubation with 5C4 antibody) and the relative proportions of retained total F protein (pre-F conformation and/or post-F conformation) (FIGS. 5B, 5D, 5F, 5H, incubation with 8C2 antibody) on viral surface in the samples treated with formaldehyde of specified concentrations for specified time periods. The results showed that after the samples were treated with formaldehyde of specified concentrations for 6 h (FIG. 5A-B), 12 h (FIG. 5C-D), 24 h (FIG. 5E-F), 36 h (FIG. 5G-H), within the same formaldehyde concentration range (e.g., 6.25% to 1.5625%, 1.5625% to 0.3906%, 0.3906% to 0.0977%, 0.0977% to 0.0244%, 0.0244% to 0.0061%), the positive value of the pre-F for 12 h treatment was relatively greater, and with the prolongation of time the sample of 12 h treatment could still maintain it at a certain level.

Furthermore, the effect of the concentration of formaldehyde on the fixation was investigated preliminarily. Formaldehyde was formulated with 1×PBS to obtain a concentration of 2 times the specified concentration (6.25%, 1.5625%, 0.3906%, 0.0977%, 0.0244%, 0.0061%, 0.0015% or 0.0004%), and allowed to stand at 25° C. for 30 min. Subsequently, the formulated formaldehyde solution and RSV were uniformly mixed at a volume ratio of 1:1 at 25° C., and inactivated at 25° C. for 12 h. Then, as described above, the fixing agent was removed by dialysis against 1×PBS. Finally, the inactivated virus was allowed to stand at 25° C. for a specified time (0 h, 24 h, 48 h, 72 h), and samples were taken at each time point for Dot blot detection.

Figure 6:
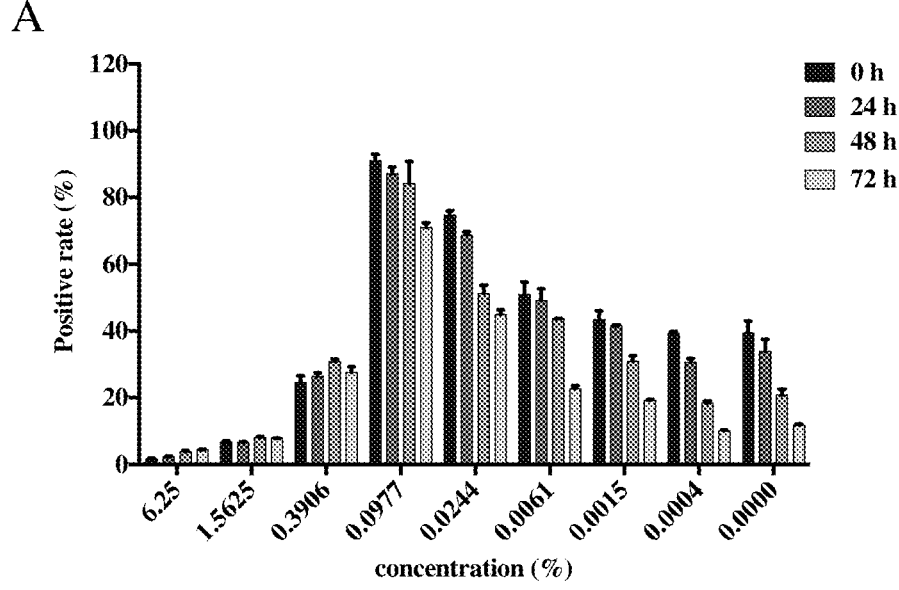
FIG. 6 shows the relative proportions of retained pre-F protein (FIG. 6A, incubation with 5C4 antibody) and the relative proportions of retained total F protein (pre-F conformation and/or post-F conformation) (FIG. 6B, incubation with 8C2 antibody) on viral surface in the samples treated with formaldehyde of specified concentrations for 12 h and stored for specified time periods.
Figure 6:
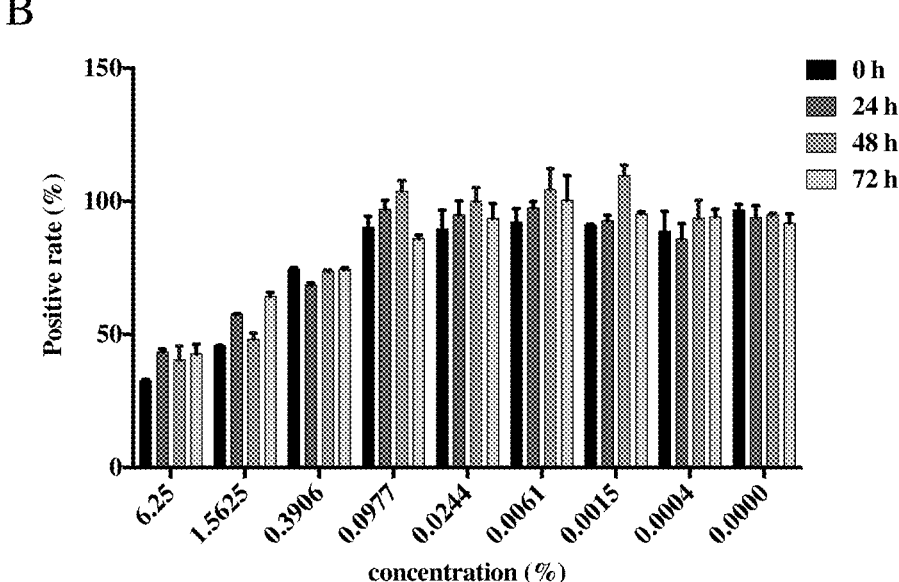

FIG. 6 shows the relative proportions of retained pre-F protein (FIG. 6A, incubation with 5C4 antibody) and the relative proportions of retained total F protein (pre-F conformation and/or post-F conformation) (FIG. 6B, incubation with 8C2 antibody) on viral surface in the samples treated with formaldehyde of specified concentrations for specified time periods. The results showed that after the samples were treated for 12 hours with formaldehyde at a concentration of 0.0244% to 0.0977%, with the extension of time (0 h, 24 h, 48 h, 72 h), a significant amount of pre-F could still be stably retained on the viral surface (that was, the conformation of pre-F protein on viral surface was stabilized and maintained). This result shows that under the condition of 12 hours of fixation and inactivation, formaldehyde with a concentration in the range of 0.0244% to 0.0977% can stabilize and maintain the conformation of pre-F protein, so that it is particularly suitable for inactivating RSV.

Figure 7:
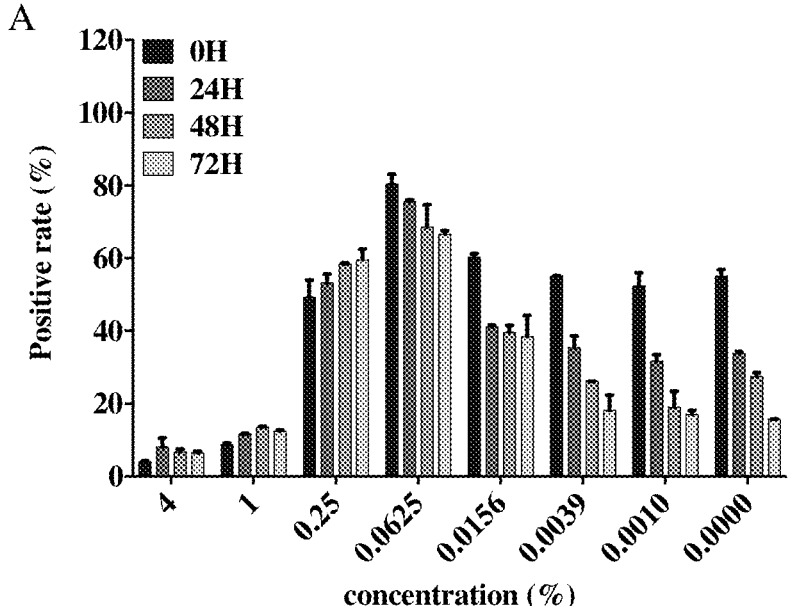
FIG. 7 shows the relative proportions of retained pre-F protein (FIG. 7A, incubation with 5C4 antibody) and the relative proportions of retained total F protein (pre-F conformation and/or post-F conformation) (FIG. 7B, incubation with 8C2 antibody) on viral surface in the samples treated with paraformaldehyde of specified concentrations for 12 h and stored for specified time periods.
Figure 7:
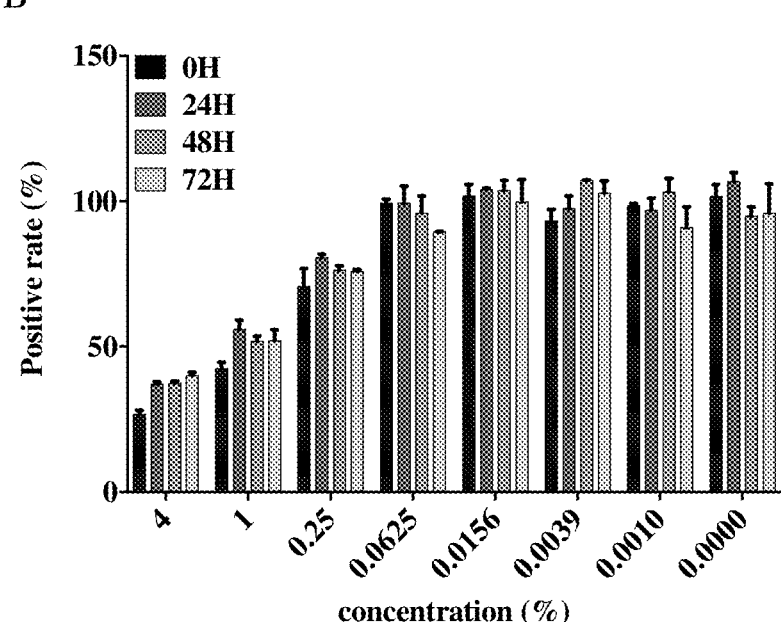

Paraformaldehyde was formulated with 1×PBS to obtain a concentration of 2 times the specified concentration (4%, 1%, 0.25%, 0.0625%, 0.0156%, 0.0039% or 0.001%), and allowed to stand at 25° C. for 30 min. Subsequently, the formulated paraformaldehyde solution and RSV were uniformly mixed at a volume ratio of 1:1 at 25° C., and then inactivated at 25° C. for 12 h. Then, as described above, the fixing agent was removed by dialysis against 1×PBS, and finally, the inactivated virus was allowed to stand at 25° C. for a specified time (0 h, 24 h, 48 h, 72 h), and samples at each time point were taken for Dot blot detection. FIG. 7 shows the relative proportions of retained pre-F protein (FIG. 7A, incubation with 5C4 antibody) and the relative proportions of retained total F protein (pre-F conformation and/or post-F conformation) (FIG. 7B, incubation with 8C2 antibody) on viral surface in the samples treated with paraformaldehyde of specified concentrations for specified time periods. The results show that after 12 hours of treatment with paraformaldehyde at a concentration of 0.0156% to 0.25%, with the extension of time (0 h, 24 h, 48 h, 72 h), a significant amount of pre-F protein could still be stably retained on viral surface (that was, the conformation of pre-F protein on viral surface was stabilized and maintained). This result shows that in the case of 12 hours of fixation and inactivation, paraformaldehyde with a concentration in the range of 0.0156% to 0.25% can stabilize and maintain the conformation of pre-F protein, so that it is particularly suitable for inactivating RSV.

In addition, the results of FIGS. 3 to 7 also show that different fixing agents have different effects on pre-F protein. In particular, the results of FIGS. 3 to 4 show that as compared with the treatment with β-propiolactone or glutaraldehyde of low concentrations, the treatment with 3-propiolactone or glutaraldehyde of high concentrations resulted in a more rapid decline in the reactivity of sample to 5C4 antibody (that was, the conformation of pre-F protein changed more quickly). These results indicate that β-propiolactone and glutaraldehyde promote the conformational change of pre-F protein. Thus, β-propiolactone and glutaraldehyde are not conducive to the maintenance and stabilization of pre-fusion conformation of RSV F protein.

In contrast, the experimental results of FIGS. 6 to 7 show that the influence of formaldehyde and paraformaldehyde on the pre-F conformation of F protein was related to their concentrations; each of them had a concentration range suitable for stabilizing pre-F protein. In particular, when formaldehyde with a concentration of 0.0244% to 0.0977% was used for fixation, the fixation time could be as long as 12 hours, and a significant amount of pre-F protein was still retained in the fixed sample. When paraformaldehyde with a concentration of 0.0156% to 0.25% was used for fixation, the fixation time could be as long as 12 hours, and a significant amount of pre-F protein was still retained in the fixed sample.

In addition, the experimental results of FIGS. 6 to 7 also show that when formaldehyde or paraformaldehyde was used at a concentration lower than the above-mentioned concentration range, the reactivity of sample to 5C4 antibody (pre-F protein) showed no significant difference compared with the unfixed group, that was, the pre-F protein on viral surface was not stably maintained. When the formaldehyde concentration reached 0.3906% or above, or the paraformaldehyde concentration reached 1% or above, the reactivity of sample to 5C4 antibody and 8C2 antibody (pre-F protein and post-F protein) was significantly reduced, which indicates that the epitopes of F protein (Pre-F and post-F) are easily destroyed by fixing agents of high concentrations.

The pre-F conformation of F protein has been confirmed to be the preferred conformation that can induce a protective antibody response against RSV. Moreover, previous studies have shown that the neutralization antibody titer induced by pre-F protein was 1 to 2 LOG higher than that of post-F protein. As analyzed above, the inactivated RSV obtained by the method of the present invention retained a significant amount of pre-F protein, so that it is particularly suitable for use as an antiviral vaccine for preventing or treating RSV infection or a disease associated with the RSV infection.

6.2 Selection of Concentration of Formaldehyde and Paraformaldehyde

Figure 8:
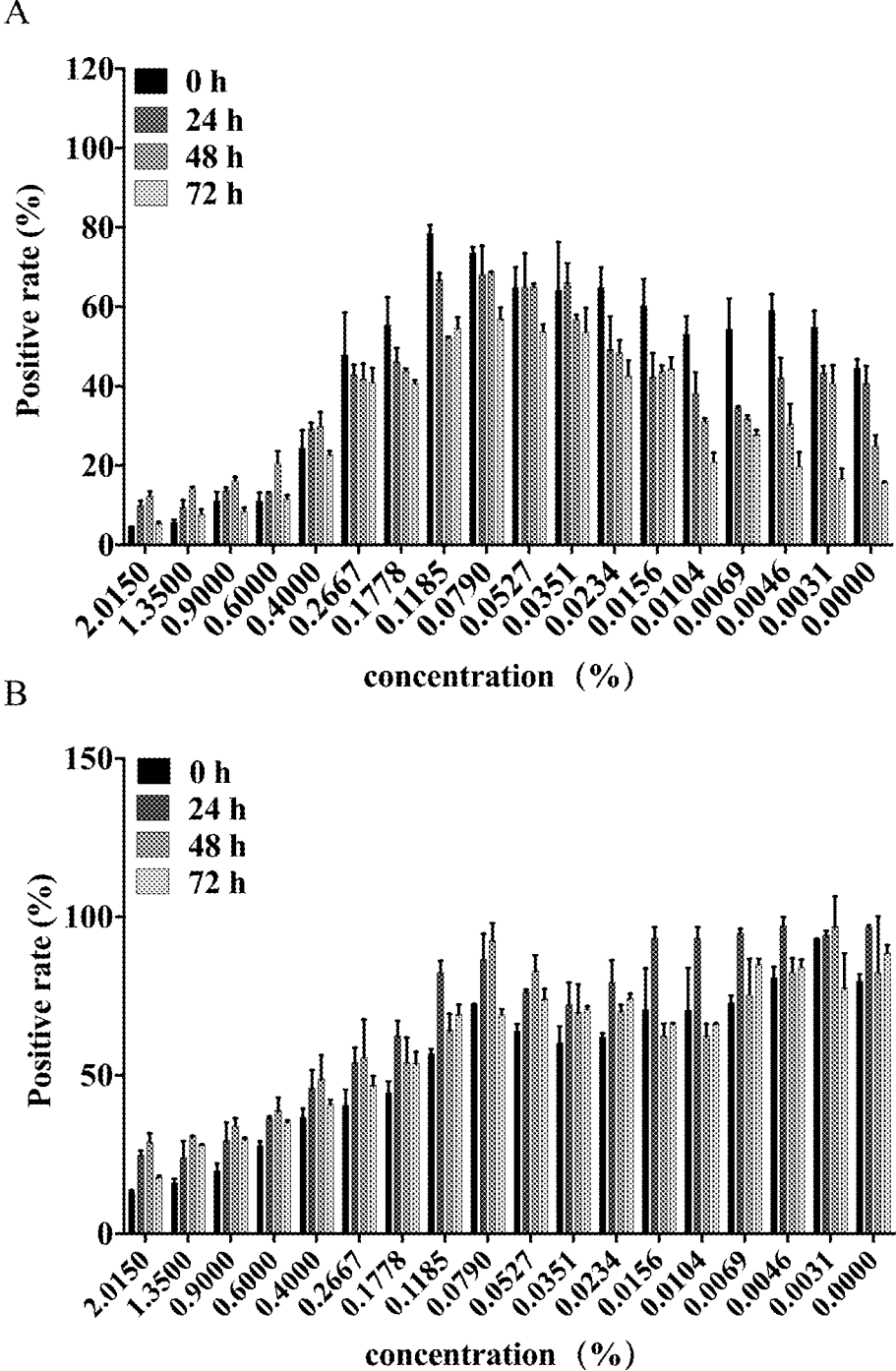
FIG. 8 shows the relative proportions of retained pre-F protein (FIG. 8A, incubation with 5C4 antibody) and the relative proportions of retained total F protein (pre-F conformation and/or post-F conformation) (FIG. 8B, incubation with 8C2 antibody) on viral surface in the samples treated with formaldehyde of specified concentrations for 12 h and stored for specified time periods.

We further studied the optimal concentration ranges of formaldehyde and paraformaldehyde. In short, formaldehyde was formulated with 1×PBS to obtain a concentration of 2 times the specified concentration (2.015%, 1.35%, 0.9%, 0.6%, 0.4%, 0.2667%, 0.1778%, 0.1185%, 0.079%, 0.0527%, 0.0351%, 0.0234%, 0.0156%, 0.0104%, 0.0069%, 0.0046%, or 0.0031%), and allowed to stand at 25° C. for 30 minutes. Subsequently, at 25° C., the formulated formaldehyde solution and RSV were uniformly mixed in a volume ratio of 1:1 for a specified time (12 h). Subsequently, as described above, the fixing agent was removed by dialysis against 1×PBS, and the inactivated virus was allowed to stand at 25° C. for a specified time (0 h, 24 h, 48 h, 72 h), and then samples were taken for Dot Blot detection. FIG. 8 shows the relative proportions of retained pre-F protein (FIG. 8A, incubation with 5C4 antibody) and the relative proportions of retained total F protein (pre-F conformation and/or post-F conformation) (FIG. 8B, incubation with 8C2 antibody) on viral surface in the samples treated with formaldehyde of specified concentrations for specified time periods.

The results showed that after the samples were treated with formaldehyde at a concentration of 0.0156% to 0.2667%, a significant amount of pre-F protein could still be stably retained on the viral surface (that was, the conformation of pre-F protein on viral surface was stabilized and maintained). This result shows that in the case of 12 hours of fixation and inactivation, formaldehyde with a concentration in the range of 0.0156% to 0.2667% can stabilize and maintain the conformation of pre-F protein, so that it is particularly suitable for inactivating RSV.

Figure 9:
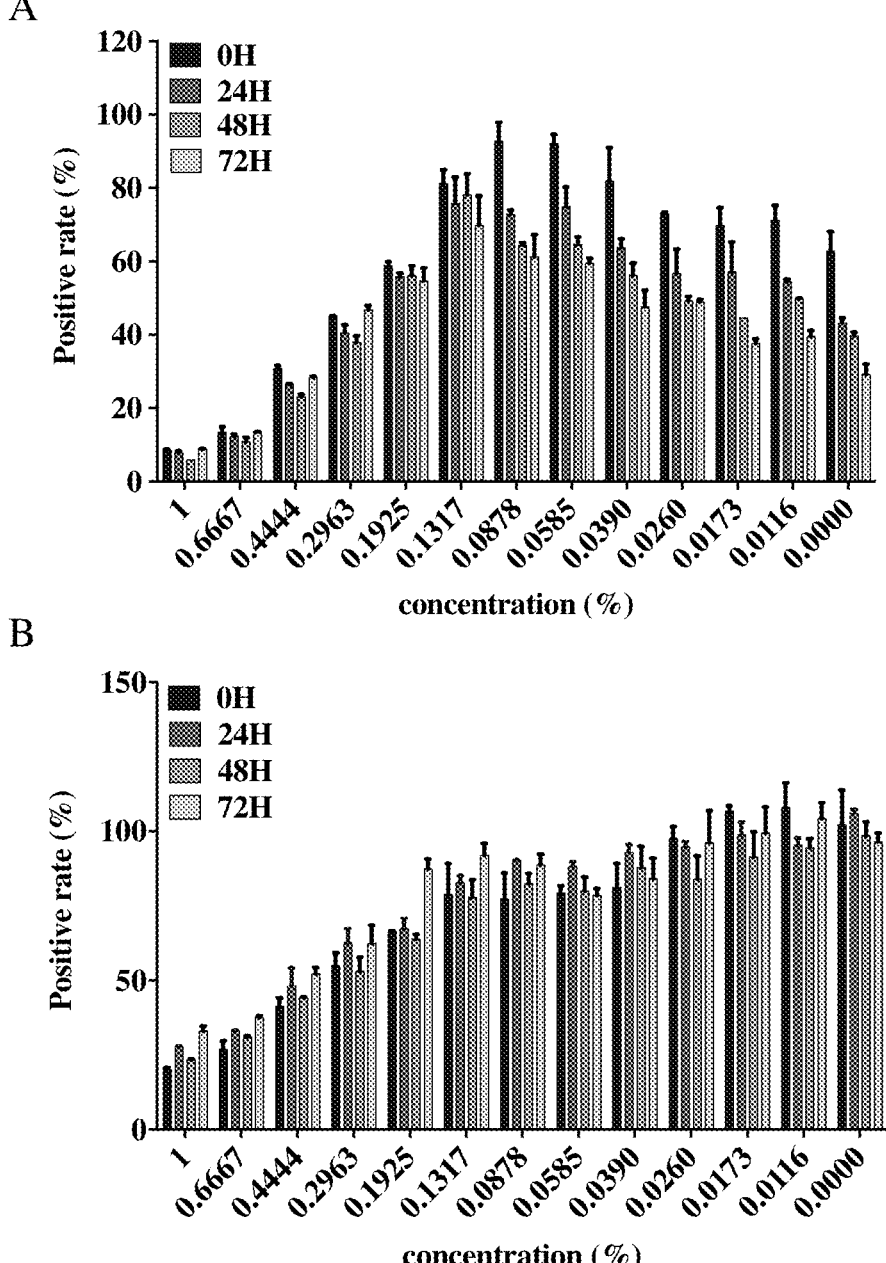
FIG. 9 shows the relative proportions of retained pre-F protein (FIG. 9A, incubation with 5C4 antibody) and the relative proportions of retained total F protein (pre-F conformation and/or post-F conformation) (FIG. 9B, incubation with 8C2 antibody) on viral surface in the samples treated with paraformaldehyde of specified concentrations for 12 h and stored for specified time periods.

In addition, paraformaldehyde was formulated with 1×PBS to obtain a concentration of 2 times the specified concentration (1%, 0.6667%, 0.4444%, 0.2963%, 0.1975%, 0.1317%, 0.0878%, 0.0585%, 0.039%, 0.026%, 0.0173%, 0.0116% or 0%), and allowed to stand at 25° C. for 30 min. Subsequently, at 25° C., the formulated paraformaldehyde solution and RSV were uniformly mixed in a volume ratio of 1:1 for a specified time (12 h). Subsequently, as described above, the fixing agent was removed by dialysis against 1×PBS, and the inactivated virus was allowed to stand at 25° C. for a specified time (0 h, 24 h, 48 h, 72 h), and then samples were taken for Dot Blot detection. FIG. 9 shows the relative proportions of retained pre-F protein (FIG. 9A, incubation with 5C4 antibody) and the relative proportions of retained total F protein (pre-F conformation and/or post-F conformation) (FIG. 9B, incubation with 8C2 antibody) on viral surface in the samples treated with paraformaldehyde of specified concentrations for specified time periods.

The results showed that after the samples were treated with paraformaldehyde at a concentration of 0.0260% to 0.2963%, a significant amount of pre-F protein could still be stably retained on the viral surface (that was, the conformation of pre-F protein on viral surface was stabilized and maintained). This result shows that in the case of 12 hours of fixation and inactivation, paraformaldehyde with a concentration in the range of 0.0260% to 0.2963% can stabilize and maintain the conformation of pre-F protein, so that it is particularly suitable for inactivating RSV.

6.3 Selection of Temperature

We further studied the effect of temperature on the fixation of fixing agent. Generally speaking, formaldehyde solution is a relatively stable fixing agent, and its fixation effect is basically not affected by temperature changes. Our experimental results had also shown that the formaldehyde solution in the preferred concentration range could be used to fix and inactivate RSV and to stabilize and maintain the pre-F protein in the inactivated virus at a temperature of 0° C. to 40° C.

Paraformaldehyde is relatively stable at low temperatures (0° C. to 10° C.), but it may degrade at a higher temperature to form formaldehyde. Therefore, paraformaldehyde is usually used under low temperature conditions (e.g., 4° C.). However, because RSV is very sensitive to temperature, the pre-F protein on its surface can easily convert into post-F protein under low temperature conditions. Therefore, in order to study the effect of paraformaldehyde on the inactivation of RSV at different temperatures, we further proceeded the following experiment.

In short, paraformaldehyde was formulated with 1×PBS to obtain a concentration of 2 times the specified concentration (4%, 1%, 0.25%, 0.0625%, 0.0156%, 0.0039% or 0.001%), and allowed to stand at a specified temperature (4° C., 25° C. or 37° C.) for 30 min. Subsequently, at the specified temperature, the formulated paraformaldehyde solution and RSV were uniformly mixed in a volume ratio of 1:1 for a specified time (e.g., 12 h). Subsequently, as described above, the fixing agent was removed by dialysis against 1×PBS, and the inactivated virus was allowed to stand at 25° C. for a specified time (0 h, 24 h, 48 h, 72 h), and then samples were taken for Dot Blot detection.

Figure 10:
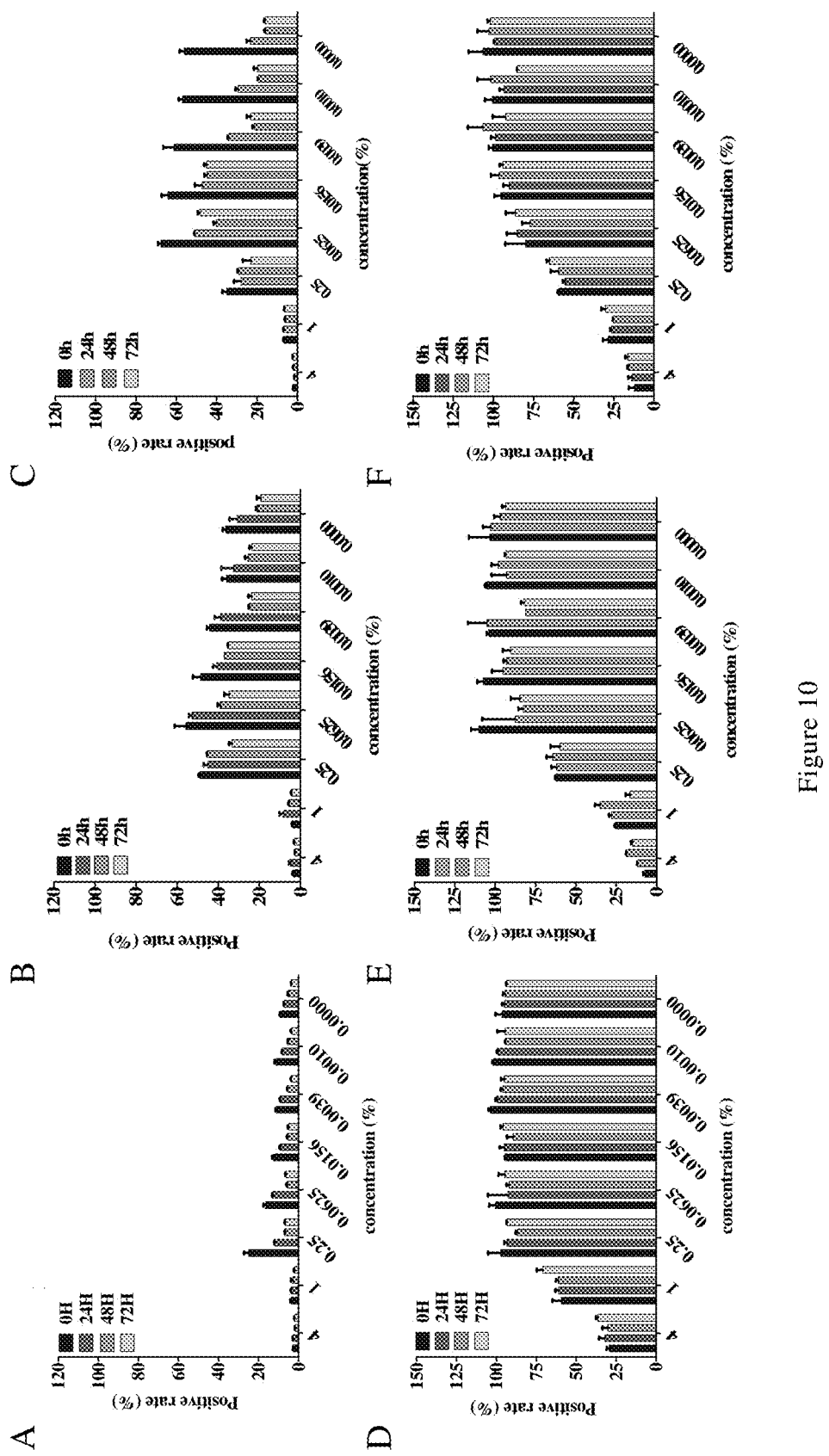
FIG. 10 shows the relative proportions of retained pre-F protein (FIGS. 10A to 10C, incubation with 5C4 antibody) and the relative proportions of retained total F protein (pre-F conformation and/or post-F conformation) (FIGS. 10D to 10F, incubation with 8C2 antibody) on viral surface in the samples treated with paraformaldehyde of specified concentrations at 4° C., 25° C. or 37° C. for 12 h and stored for specified time periods.

The experimental results are shown in FIG. 10. FIG. 10 shows the relative proportions of retained pre-F protein (FIGS. 10A to 10C, incubation with 5C4 antibody) and the relative proportions of retained total F protein (pre-F conformation and/or post-F conformation) (FIGS. 10D to 10F, incubation with 8C2 antibody) on viral surface in the samples treated with paraformaldehyde of specified concentrations at 4° C. (A, D), 25° C. (B, E) or 37° C. (C, F) for specified time periods.

The results showed that after the samples were treated with paraformaldehyde at a concentration of 0.001% to 4% at 4° C., the pre-F protein on viral surface in the samples was almost completely undetectable (that was, it failed to stabilize and maintain pre-F protein conformation, and even accelerated or promoted the conformational change of pre-F protein). After the samples were treated with paraformaldehyde at a concentration of 0.0156% to 0.25% at 25° C., a significant amount of pre-F protein could be stably retained on the viral surface (that was, the conformation of pre-F protein on the viral surface was stabilized and maintained). After the samples were treated with paraformaldehyde at a concentration of 0.0156% to 0.0625% at 37° C., the sample still contained a significant amount of pre-F protein-positive cells (that was, the conformation of pre-F protein in the samples was stabilized and maintained).

These results show that paraformaldehyde may play its role (that was, inactivation of RSV, and stabilization and maintenance of pre-F protein in virus) at different temperatures, but its preferred concentration range should be appropriately adjusted according to the actually used temperature. However, most preferably, paraformaldehyde is used under normal temperature conditions (10° C. to 37° C.) to fix and inactivate the RSV and stabilize and maintain the pre-F protein.

6.4 Detection of Stability of Pre-F Protein on Viral Surface of the Fixed Sample We further studied the stability of pre-F protein on viral surface in the fixed sample. In short, formaldehyde was formulated with 1×PBS to obtain a concentration of 2 times the specified concentration (e.g., 25%, 6.25%, 1.5625%, 0.3906%, 0.0977%, 0.0244%, 0.0061%, 0.0015% or 0.0004%), and allowed to stand at 25° C. for 30 minutes. Subsequently, at 25° C., the formulated formaldehyde solution and RSV were uniformly mixed in a volume ratio of 1:1 for 12 hours. Subsequently, dialysis against PBS salt solution was performed to remove the fixing agent and preserve the fixed samples in PBS salt solution. In addition, a sample that was not treated with fixing agent was preserved in physiological saline buffer and used as a control. Then, after standing at room temperature for a specified time (0 h, 24 h, 48 h or 72 h), the fixed samples were used for Dot blot detection.

Figure 11:
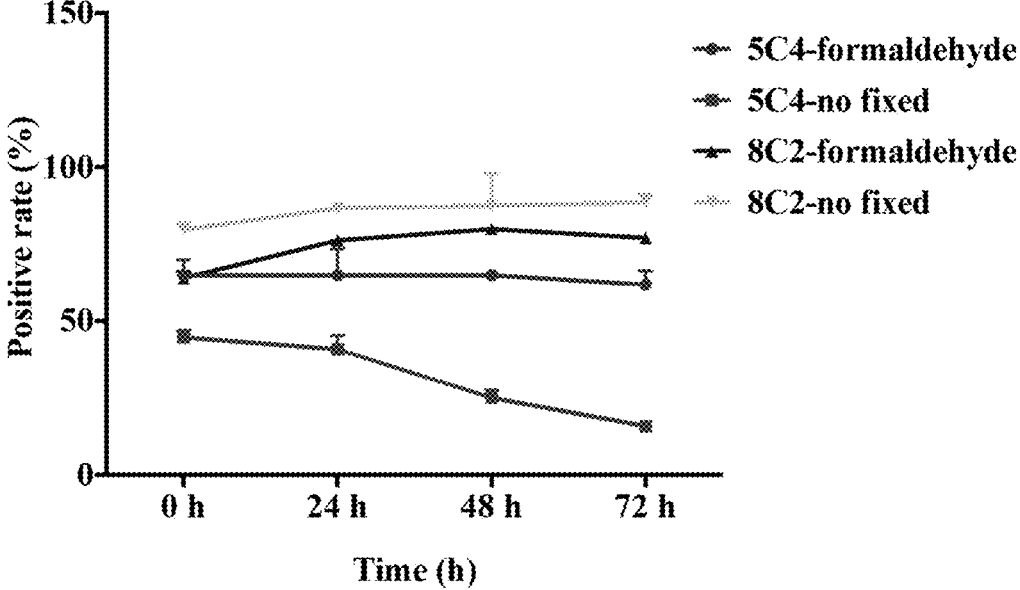
FIG. 11 shows the change over time in the relative proportion of pre-F protein retained on viral surface in the samples treated with formaldehyde and preserved in PBS solution and in the sample that has not been treated with fixing agent.

The experimental results are shown in FIG. 11. FIG. 11 shows the change over time in the relative proportion of pre-F protein retained on viral surface (incubation with 5C4 antibody) in the samples treated with formaldehyde and preserved in PBS solution and in the sample untreated with fixing agent.

The results showed that after being preserved for up to 72 hours, a significant amount of pre-F protein was retained on viral surface in the formaldehyde-treated samples (that was, the pre-F protein on viral surface in the samples remained stable and did not undergo conformational change). In contrast, after being preserved for 24 hours, the amount of pre-F protein retained on viral surface in the sample without being treated with fixing agent decreased with the extension of standing time. These results indicate that the method for fixing and inactivating RSV of the present invention can effectively stabilize the pre-F protein on the surface of the RSV and prevent it from being transformed into post-F protein.

Example 2. Preservation of RSV

In this example, we further studied the effect of dialysis salt solution (i.e., storage solution) on the pre-F protein on viral surface after fixation. Generally speaking, we used dialysis, filtration or centrifugation to remove fixing agent in a fixed sample (i.e., a solution comprising inactivated virus and fixing agent). In Example 1, we used the method of placing the fixed sample in a dialysis salt solution of different concentrations to replace the fixing agent, so as to preserve the inactivated virus in the corresponding storage solution. In this example, the fixed sample was further dialyzed against different salt solutions to monitor the stability of the inactivated/fixed viral protein over time in different salt solutions, thereby selecting a more suitable storage salt solution environment to make the pre-F protein on viral surface more stable.

Sodium chloride (NaCl, Sodium chloride), (AR) (Xilong Chemical Industry, 10011012AR) and disodium hydrogen phosphate dodecahydrate (Sinopharm Group, 325) were used under a molar concentration ratio of 10:1 to prepare salt solutions of different concentrations (330 mM, 550 mM, 880 mM). PBS solution was also used as one kind of solution, the molar concentration of which was calculated to be about 150 mM.

The obtained inactivated/fixed sample was placed in a dialysis bag, and then placed in different salt solutions for dialysis, and the dialysis conditions were: 25° C., 300 rpm, and the volume ratio of sample to dialysate was 1:500, the dialysis time was 18 h, and the liquid was replaced at 3 h, 6 h and 12 h respectively.

The dialyzed sample was taken and placed in an EP tube of appropriate volume. After being allowed to stand at 25° C. for a certain period of time (e.g., 0 h, 24 h, 48 h, 72 h), the viral surface F protein was detected to monitor the changes over time in the pre-F protein and the total F protein on viral surface in different salt solutions.

Figure 12:
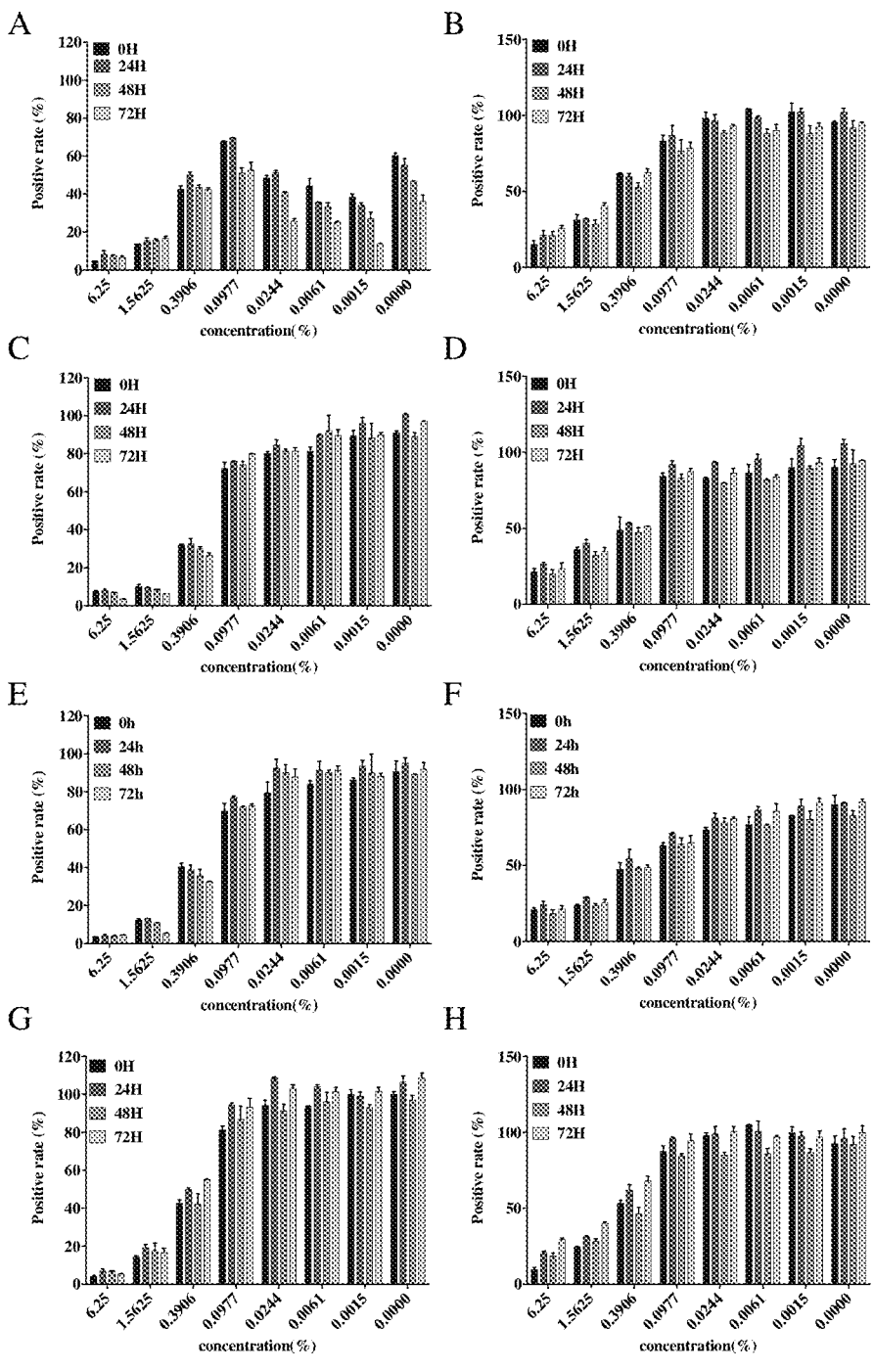
FIG. 12 shows the relative proportions of retained pre-F protein (FIGS. 12A to 12D, incubation with 5C4 antibody) and the relative proportions of retained total F protein (pre-F conformation and/or post-F conformation) (FIGS. 12E to 12H, incubation with 8C2 antibody) on viral surface with the extension of storage time after the inactivated/fixed viruses were dialyzed in salt solutions of 150 mM, 330 mM, 550 mM, 880 mM.

The experimental results are shown in FIG. 12. FIG. 12 shows the relative proportions of retained pre-F protein (FIGS. 12A, 12C, 12E, 12G, incubation with 5C4 antibody) and the relative proportions of retained total F protein (pre-F conformation and/or post-F conformation) (FIGS. 12B, 12D, 12F, 12H, incubation with 8C2 antibody) on viral surface with the extension of standing time after the inactivated/fixed viruses were dialyzed in salt solutions of 150 mM (A, B), 330 mM (C, D), 550 mM (E, F), 880 mM (G, H).

The results showed that after dialysis in salt solution of 150 mM, the virus fixed with the preferred fixing agent concentration retained more pre-F protein on its surface, and with the extension of standing time, the pre-F protein on viral surface was kept at a high level, and can be maintained for more than 72 h. However, for the virus that was fixed under a condition of concentration lower or higher than the preferred fixing solution concentration range, a large amount of the pre-F protein on its surface was lost, and with the extension of standing time in the salt solution, more of the pre-F protein on viral surface was lost. After dialysis in salt solutions of 330 mM, 550 mM, 880 mM, for the virus fixed under a condition of concentration equal to or higher or lower than the preferred fixing solution concentration, a large amount of pre-F protein on its surface was retained, which increased with the increase of the salt solution concentration and gradually approached 90% to 100%, and this high level of protein could be stably maintained for more than 72 hours.

The above results indicate that in the process of removing the fixing agent from the fixed/inactivated virus by dialysis, the salt ion concentration of the dialysate (that was, the storage solution of the fixed/inactivated virus) is important for stabilizing or maintaining the conformation of the pre-F protein on viral surface. When using a salt solution with a lower ion concentration (e.g., a salt ion concentration of less than 150 mM) as a storage solution, during dialysis or storage, the pre-F protein on viral surface will rapidly convert into post-F protein with the extension of dialysis or storage time. When using a salt solution with a higher ion concentration (e.g., a salt ion concentration of not less than 150 mM) as a storage solution, with the extension of dialysis or standing time, the virus inactivated under the preferred fixation/inactivation conditions (e.g., formaldehyde or paraformaldehyde at their preferred concentrations as described in Example 1) can be preserved in the salt solution to well maintain the fixed pre-F protein; for the virus inactivated under non-preferred fixation/inactivation conditions (e.g., lower than the preferred concentration as described in Example 1, and/or non-preferred fixing agent) and even unfixed virus, the unfixed pre-F protein could be kept in pre-F conformation during dialysis or storage in high salt concentration solution, making it difficult to undergo conformational change. Therefore, a solution with a higher ion concentration (e.g., no less than 150 mM) can well stabilize the pre-F protein conformation, and thus it is particularly suitable for the preservation of RSV.

Example 3. Detection of Immune Protection

In this example, we investigated the immunoprotection of RSV treated with formaldehyde fixing agent. In short, formaldehyde was formulated with 2×PBS to get a concentration of 0.01% or 0.0527%, and allowed to stand at 25° C. for 30 min. Subsequently, at 25° C., the formulated formaldehyde solution and the virus were mixed slowly until homogeneous at a volume ratio of 1:1 for 12 hours. Subsequently, as described above, the fixing agent was removed by dialysis (for 18 hours at 25° C.), the dialysate was salt solution of 550 mM. Then the dialyzed sample was centrifuged to remove a portion of soluble contaminants, and the precipitate was resuspended and mixed with a certain volume of serum-free medium and mixed well with AL adjuvant at a volume ratio of 1:1, which was used for immunization by intramuscular injection in SPF Balb/C mice (n=6-10). The groups of inactivation with 0.0527% formaldehyde had three immunization doses, which were $2.52 \times 10^5$ (L), $2 \times 10^7$ (M) and $1 \times 10^8$ (H) virus particles/mouse, and the group of inactivation with 0.01% formaldehyde had an immunization dose of $2.52 \times 10^5$ virus particles/mouse, and the immunization cycle was once every 15 days for a total of 2 times. Fifteen days after the end of each injection, blood samples were collected from the mice by eyeball sampling method and used to detect the level of neutralization antibodies in serum.

The level of neutralization antibodies in serum was detected by the following protocol. The mouse serum was diluted with culture medium in a 96-well plate (SIGMA-ALDRICH), in which the first well of each serum was diluted 10 times (90 μl medium+10 μl serum), and the rest wells were diluted 4 times (75 μl medium+25 μl dilution serum), for a total of 9 dilution gradients. 75 μl of diluted serum and 75 μL of RSV-A mkate virus with a titer of $2 \times 10^6$ PFU (this virus could express fluorescent protein mkate in the infected cells, and the intensity of infection could be finally judged by fluorescence intensity of mkate). The diluted serum and virus were mixed and incubated at 37° C. for 1 hour. One hour later, 100 μl of the mixed solution of serum and virus was taken and added into a 96-well cell plate pre-plated with Hep-2 cells (ATCC) ($5 \times 10^4$ cells per well). After the cell plate was incubated at 37° C. for 24 hours, the fluorescence value was read with PARADIGM multi-function plate reader (BECKMAN COULTER). For each serum, a set of fluorescence readings was obtained after the cells were infected with virus under different dilution concentrations. The fluorescence readings and serum dilution degrees were input into Graph Prism software, and the neutralization IC50 of each serum was calculated by curve fitting. In the experiment, 8C2 monoclonal antibody was also used for neutralization detection as a control. Finally, based on the IC50 data, the IC50 titer relative to 8C2 was converted for each serum, and by taking 8C2 antibody of 1 mg/mL as one neutralization unit, and the neutralization unit relative to 8C2 for each serum was output.

Figure 13:
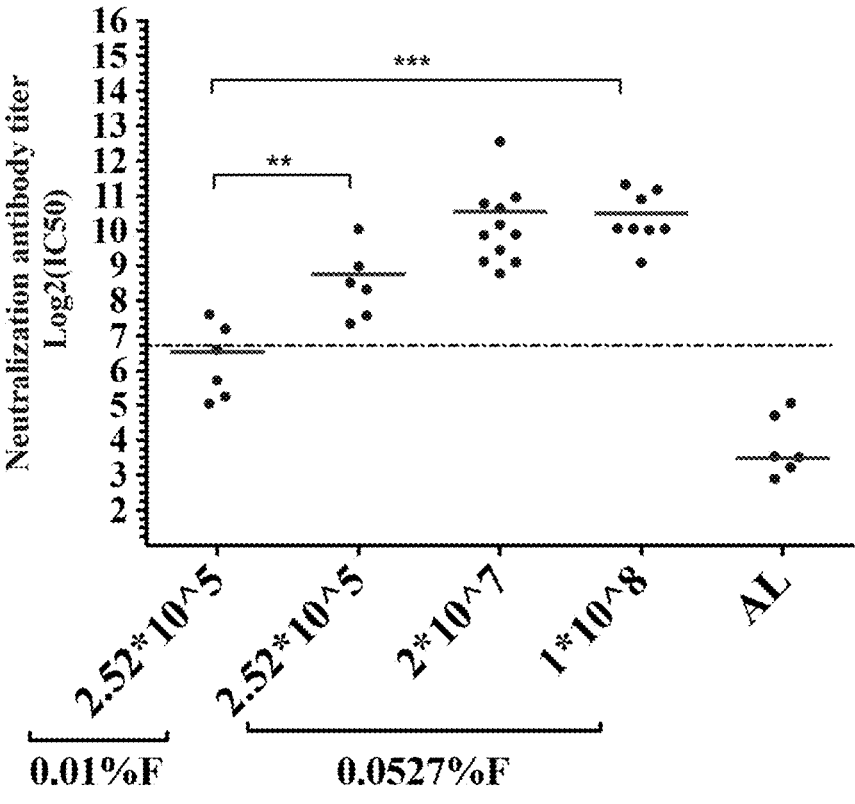
FIG. 13 shows the detection results of RSV-specific neutralization antibody levels in mice after immunization with the viruses inactivated by using a formaldehyde solution of a preferred concentration and a formaldehyde solution of a non-preferred concentration as immunogen.

The experimental results are shown in FIG. 13. FIG. 13 shows the detection results of RSV-specific neutralization antibody levels in mice after immunization with the viruses inactivated by using a formaldehyde solution of a preferred concentration (i.e., 0.0527%) and a formaldehyde solution of a non-preferred concentration (i.e., 0.01%) as immunogen.

The ordinate in FIG. 13 represents the IC50 value of mouse serum neutralization antibody after the second immunization injection. The results show that the viruses inactivated by formaldehyde solution of different concentrations could stimulate different levels of RSV neutralization antibody under the same immunization dose. In the comparison between the viruses inactivated under concentrations of 0.01% and 0.0527%, the virus inactivated under the preferred condition (0.0527% formaldehyde) as immunogen could induce a higher level of neutralization antibody, and there were statistical differences. In addition, with the increase of the immunization dose, the level of neutralization antibody as induced also increased. These results indicate that the inactivated RSV obtained by the method of the present invention retains a significant amount of pre-F protein, thereby inducing a high titer of neutralization antibody. Therefore, it is particularly suitable for use as an antiviral vaccine for the prevention or treatment of RSV infection or a disease associated with the RSV infection.

Although the specific embodiments of the present invention have been described in detail, those skilled in the art will understand that various modifications and changes can be made to the details according to all the teachings that have been disclosed, and these changes are all within the protection scope of the present invention. The full scope of the present invention is given by the appended claims and any equivalents thereof.

What is claimed is:

1. A method for inactivating an isolated respiratory syncytial virus (RSV) and stabilizing a pre-F protein in the RSV, which comprises the following steps:

(1) providing an isolated live RSV, in which the isolated live RSV is not contained in a cell or not provided in a cell in any other ways;

(2) fixing and inactivating the live RSV (i) by using a fixing agent which is a formaldehyde solution having a formaldehyde concentration of about 0.0351% to about 0.1185% by weight (w/w, the same hereinafter) at a temperature of about 0° C. to about 40° C. and for a duration of about 6h to about 12h; or (ii) by using a fixing agent which is a paraformaldehyde solution with a concentration of about 0.015% to about 0.25% by weight (w/w, the same hereinafter) at a temperature of about 20° C. to about 30° C. for a duration of about 6h to about 12h, or a paraformaldehyde solution with a concentration of about 0.0156% to about 0.0625% by weight (w/w, the same hereinafter) at a temperature of about 35° C. to about 40° C. for a duration of about 6h to about 12h;

(3) removing the fixing agent from the product of step (2), thereby obtaining an inactivated RSV.

2. The method according to claim 1, wherein in step (1), the isolated live RSV is provided by the following steps: (1a) infecting a host cell with a RSV; (1b) culturing the infected host cell obtained in step (1a) under a condition that allows the propagation of the RSV; and (1c) collecting and lysing the cultured host cell obtained in step (1b), and recovering the RSV from a lysate thereof;

and, the product of step (1c) does not comprise the host cell.

3. The method according to claim 1, wherein in step (3), the fixing agent is removed by dialysis, filtration or centrifugation.

4. The method of claim 1 further comprising preserving a RSV and stabilizing a pre-F protein in the RSV, which comprises a step of placing the RSV in a storage solution, wherein the storage solution is a salt solution having an ion concentration of about 150 to about 1000 mM.

5. The method according to claim 4, wherein the RSV is dialyzed against a salt solution for a duration of about 6 h to about 24 h, thereby placing the RSV in a storage solution; wherein the salt solution has an ion concentration of about 150 to about 1000 mM.

6. The method according to claim 4, wherein the RSV is an inactivated virus;

and the inactivated RSV is provided through the following steps:

(i) providing an isolated live RSV;

(ii) fixing and inactivating the live RSV by using a fixing agent;

(iii) removing the fixing agent from the product of step (ii), thereby obtaining an inactivated RSV.

7. The method according to claim 6, which comprises the following steps:

(1) providing an isolated live RSV;

(2) fixing and inactivating the live RSV by using a fixing agent;

(3) dialyzing the product of step (2) by using a salt solution to obtain a storage solution containing the inactivated RSV;

wherein in step (3), the salt solution has an ion concentration of about 150 to about 1000 mM;

and step (2) is characterized by one of the following: (a) the live RSV is fixed and inactivated by using a formaldehyde solution having a formaldehyde concentration of not greater than about 0.27% by weight at a temperature of about 0° C. to about 40° C. and/or for a duration of about 6h to about 36h; or, (b) the live RSV is fixed and inactivated by using a paraformaldehyde solution having a paraformaldehyde concentration of not greater than about 0.3% by weight at a temperature of about 10° C. to about 40° C. and/or for a duration of about 6h to about 36h.

8. The method according to claim 4, which further comprises a step of preserving the storage solution containing RSV at a temperature of about 0° C. to about 40° C.

9. A vaccine, which comprises an inactivated RSV which is prepared by the method of claim 1, and a pharmaceutically acceptable carrier and/or excipient.

10. A method for prevention, treatment or inhibition of RSV infection or a disease associated with RSV infection in a subject, which comprises administering an effective amount of the vaccine according to claim 9 to a subject in need thereof.

11. The method of claim 1, wherein in step (2), the live RSV is fixed and inactivated by using a paraformaldehyde solution with a concentration of about 0.015% to about 0.25% at a temperature of about 20° C. to about 30° C. for a duration of about 6h to about 12h; or, the live RSV is fixed and inactivated by using a paraformaldehyde solution with a concentration of about 0.02% to about 0.0625% at a temperature of about 35° C. to about 37° C. for a duration of about 6h to about 12h.

12. The method of claim 3, in step (3), the product of step (2) is dialyzed against a salt solution to remove the fixing agent, and the salt solution has an ion concentration of about 100 to about 1000 mM.

13. The method of claim 4, wherein the inactivated RSV is placed in the storage solution by dialysis, filtration or centrifugation.

14. The method of claim 6, wherein in step (ii), the fixing agent is selected from the group consisting of formaldehyde solution, paraformaldehyde solution, glutaraldehyde solution and β-propiolactone solution.

15. The method of claim 6, wherein the inactivated RSV is provided by a method comprising:

(1) providing an isolated live RSV;

(2) fixing and inactivating the live RSV by using a fixing agent selected from the group consisting of: a formaldehyde solution having a formaldehyde concentration of about 0.015% to about 0.27% by weight (w/w, the same hereinafter) and a paraformaldehyde solution having a paraformaldehyde concentration of about 0.02% to about 0.3% by weight (w/w, the same hereinafter);

(3) removing the fixing agent from the product of step (2), thereby obtaining an inactivated RSV.

16. A vaccine, which comprises an inactivated RSV which is preserved by the method of claim 6, and a pharmaceutically acceptable carrier and/or excipient.

17. A method for prevention, treatment or inhibition of RSV infection or a disease associated with RSV infection in a subject, which comprises administering an effective amount of the vaccine according to claim 16 to a subject in need thereof.

18. The method of claim 10, wherein the disease associated with RSV infection is a pneumonia.

19. The method of claim 17, wherein the disease associated with RSV infection is a pneumonia.

\* \* \* \* \*